United States Patent [19]

Bro

[11] Patent Number: 5,377,258
[45] Date of Patent: Dec. 27, 1994

[54] METHOD AND APPARATUS FOR AN AUTOMATED AND INTERACTIVE BEHAVIORAL GUIDANCE SYSTEM

[75] Inventor: William L. Bro, Los Angeles, Calif.
[73] Assignee: National Medical Research Council, Santa Monica, Calif.
[21] Appl. No.: 112,955
[22] Filed: Aug. 30, 1993
[51] Int. Cl.$^5$ .................... H04M 1/64; H04M 11/00
[52] U.S. Cl. ...................................... 379/93; 379/92; 379/67; 379/88
[58] Field of Search ................. 379/93, 94, 96, 97, 379/98, 67, 68, 69, 88, 89, 90, 92; 128/903, 904; 364/413.02, 413.03, 413.04

[56] References Cited

U.S. PATENT DOCUMENTS

| | | |
|---|---|---|
| 3,742,938 | 7/1973 | Stern . |
| 3,808,694 | 5/1974 | Hutchinson et al. . |
| 4,112,425 | 9/1978 | Zobrist et al. ........... 340/347 |
| 4,237,344 | 12/1980 | Moore . |
| 4,328,494 | 5/1982 | Goodall ............... 340/870.18 |
| 4,377,214 | 3/1983 | Hansen et al. ........... 364/466 |
| 4,396,976 | 8/1983 | Hyatt .................. 364/167 |
| 4,602,127 | 7/1986 | Neely et al. . |
| 4,773,492 | 9/1988 | Ruzumna ................ 177/25 |
| 4,831,242 | 5/1989 | Engelhardt et al. ........ 235/382 |
| 4,835,372 | 5/1989 | Gombrich et al. ......... 379/93 |
| 4,912,552 | 3/1990 | Allison, III et al. ....... 358/84 |
| 4,916,435 | 4/1990 | Fuller ................. 340/573 |
| 4,922,514 | 5/1990 | Bergeron et al. .......... 379/6 |
| 4,922,520 | 5/1990 | Bernard et al. .......... 379/97 |
| 4,933,873 | 6/1990 | Kaufman et al. .......... 364/513.5 |
| 4,952,928 | 8/1990 | Carroll et al. .......... 128/903 |
| 5,008,835 | 4/1991 | Jackmann et al. ......... 364/513.5 |
| 5,014,298 | 5/1991 | Katz .................. 379/93 |
| 5,018,736 | 5/1991 | Person et al. .......... 379/93 |
| 5,023,901 | 6/1991 | Sloan et al. ........... 379/38 |
| 5,036,462 | 7/1991 | Kaufman et al. .......... 364/413.01 |
| 5,068,080 | 11/1991 | Impink, Jr. et al. ....... 376/215 |
| 5,085,527 | 2/1992 | Gilbert ................ 374/14 |

OTHER PUBLICATIONS

"The Vulnerable Body Image of Females with Feelings of Depression" by Mori & Morey.
"Selective Recall of Positive and Negative Feedback . . ." by Nelson & Craighead, 1977.
"The Psychology of Perception" by W. Freeman Feb. 1991.
"Olfactory stimuli as context cues in human memory" by Cann a & Ross, spring 1989.
"Odors and the Remembrance of Thins Past"]by F. Schab 1990.
"Encoding Specificity and Retrieval Process in Episodic Memory" by Tulving & Thompson, 1973.
"Gender and Vocal Stress Differences During Truthful and Deceptive Information Sequences" by O'Hair & Cody, 1987.
"Quantitative EEG Analysis During Hypnosis" by Ulett, Akpinar & Itil, 1972.
"Response to Leaflets About Eating and Shape by Women Concerned Videodisc based Instruction" by Kearsley & Frost, Mar. 1985.
"Lights, Camera, Reaction! The Interactive Videodisc: A Tool for Teaching Chemistry" by Jones and Smith, Mar., 1989.
"In Search of How People Change", by Prochaska, DiClemente & Norcross, Sep. 1992.

Primary Examiner—Curtis Kuntz
Assistant Examiner—Jason Chan
Attorney, Agent, or Firm—Cislo & Thomas

[57] ABSTRACT

An automated and interactive positive motivation system (10) that allows a doctor or trainer to produce and send a series of motivational messages and/or questions to a client (50) to motivate or reinforce a specific behavioral problem. The system (2) consists of a client database (12) that includes for each client the name, calling schedule and personal identification number (PIN) and a client program (14) that includes for each client unique motivational messages and/or questions which can be used alone or with such devices as an electronic weight scale (38), olfactory unit (40), and voice stress analyzer (42) that require a client response. The database and program are operated by a computer (16) that at preselected time periods sends the messages and/or questions to a client's dual tone multifrequency telephone set (26) via a digital/telephone tone signal converter (18) and a telephone network (24). Before the messages and/or questions are sent, the client must transmit to the computer (16) via the telephone set (26), a valid PIN.

39 Claims, 3 Drawing Sheets

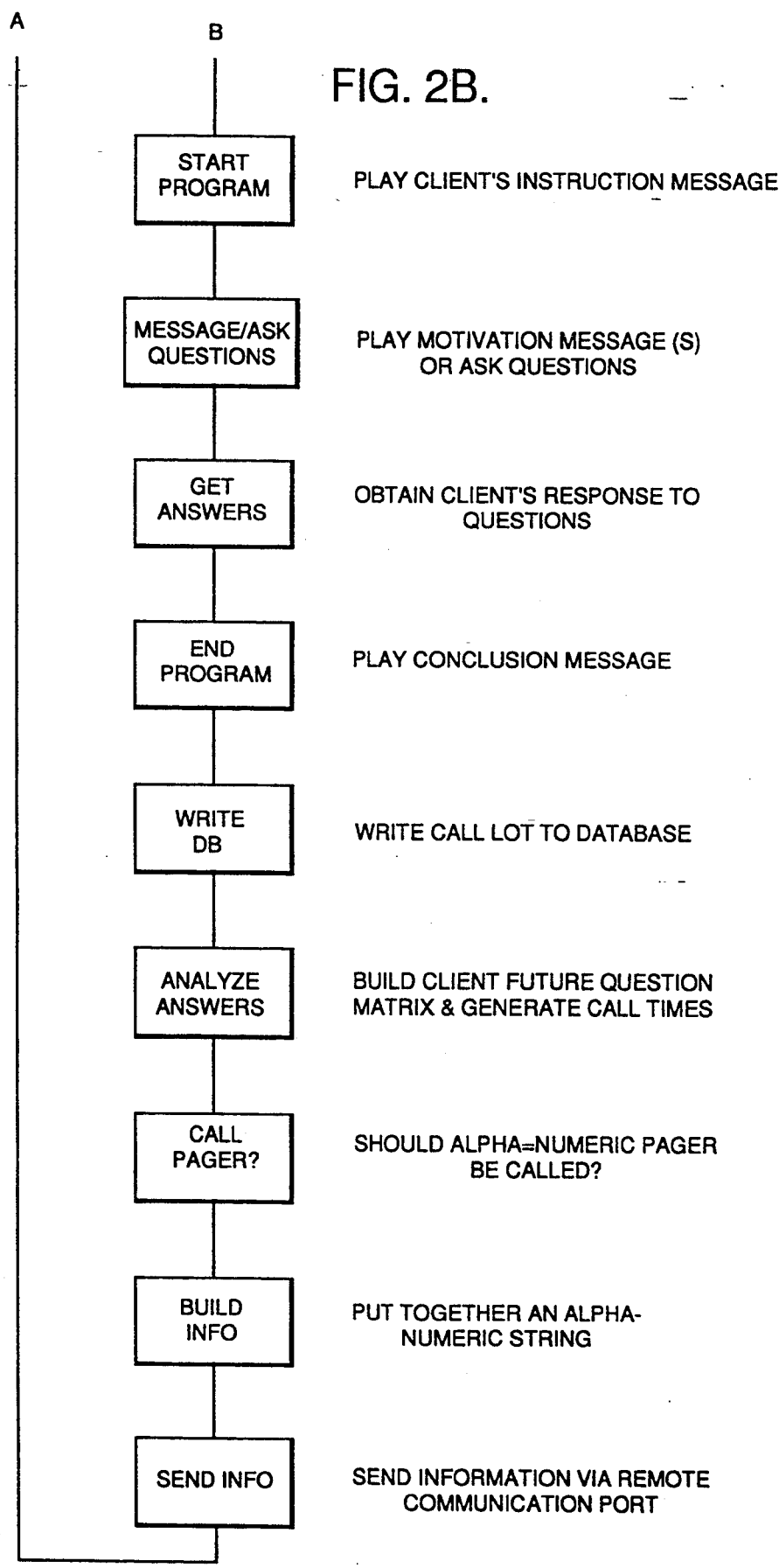

METHOD AND APPARATUS FOR AN AUTOMATED AND INTERACTIVE BEHAVIORAL GUIDANCE SYSTEM

TECHNICAL FIELD

The invention pertains to the general field of information exchange services, education and personal health care and more particularly to a computerized telephonic system that conveys health awareness messages and maintains surveillance over clients by periodically sending behavioral motivation reinforcement messages and/or questions that require a client interaction.

BACKGROUND ART

One of the major advances of present-day society is in the field of computerized telecommunications. Today, in the growing field of behavioral medicine, formal verbal interchange is essential to provide modification of behavior and reinforcement. By using computerized telecommunications coupled with voice recognition technology, a client's behavior can be modified and reinforced at the site where behavior occurs and wherever the client goes. It has been found that as the frequency of reinforcing feedback increases, the client shows more rapid progress towards a particular goal. By utilizing a system of continuous computerized reinforcement, a client can be provided with more opportunity and greater frequency of therapeutic contact or feedback than through treatment in person. Additionally, the use of an interactive system vastly increases the therapeutic effect of this method of behavioral modification and reinforcement.

Learning is enhanced through interactive feedback, and feedback in some form heightens the learning experience. The number of times in school a teacher asks any one child for an answer is fairly limited. Most of the time, children raise their hands and respond, and get back a "right" or "wrong." If they are wrong, they have lost their chance, and someone else is called upon for the answer. In traditional adult education and behavioral modification, the amount of continuing feedback is limited to the time actually spent with a counselor or in a seminar. Here, too, the feedback is limited to the actual time the counselor or trainer spends providing interaction with any one client. By contrast, the addition of a computer and telecommunications or broadcast transmission allows "narrowcast" interaction and feedback on a continuous 24-hour basis to the client wherever he goes, allowing for far greater frequency of interaction. Most importantly, in the case of adult behavior modification, this feedback becomes available for the first time at the site where the behavior occurs.

Learning by playing and doing is fundamental to all mammals. While audio broadcast or telecommunications are media based upon hearing, and video broadcast is a medium based upon seeing, interactive feedback utilizing these architectures is a medium based upon doing or responding to the stimulus of feedback. Recent studies have revealed that the single best way to increase mammalian intelligence is through interactive stimulation. The frequency of feedback that we receive generally is the single greatest factor affecting learning and modifying behavior. Further, learning by receiving immediate feedback is preferable to receiving a delayed response. Children prefer interactive television games to merely watching a television program. They become impatient with long strings of dialogue, and the focus of their attention is diverted by devices providing rapid feedback. Adults display the same behavior throughout their lives. For example, when purchasing an appliance, they rarely read the instructions before trying to use it. The need to receive continuing feedback, at all levels of life, is a human characteristic, thus providing a basic survival mechanism which fosters learning and continuing growth.

Research indicates that learning is enhanced by interactive feedback. Where the quantity of interacting feedback is increased, focus is sustained or increased, thereby stimulating keen responsiveness, as is the case with video games. The active involvement required to respond by answering provocative questions stimulates conscious awareness of and focus on the issue at hand. Learning and behavioral modification systems that incorporate rapid feedback foster problem-solving abilities, pattern recognition, management and allocation of resources, logical thinking patterns, memory, quick thinking, and reasoned judgment. Most importantly, when these skills are practiced at the site where the desired behavior is to occur, learning is more vivid and is quickly integrated into real life.

A sense of control is perceived with the provision of feedback. By engaging the client to direct his focus and asking provoking questions, involvement is increased and stimulation results. When the individual learner achieves success and immediately receives positive feedback, self-esteem is rapidly built. When success is rewarded, confidence and resilience are enhanced and knowledge is created.

Historically, individuals have sought self-improvement through self-help books, seminar workshops and programs of a periodic or short duration. With the best of intentions relapse usually occurs within several days after reading a book or attending a seminar, or several months after the conclusion of a behavioral modification program.

In contrast, computer-derived, self-adjusting motivational guidance, which interactively polls the client and comments on his performance as he goes about his daily life throughout the year, has a more lasting effect. It differs importantly from seminars and visits to counselors in that it modifies behavior at the site where the behavior occurs, with personal or customized intervention. The more frequent interactive dialogue between the counselor-controlled computer and the client enhances the feedback and therapeutic simulation in much the same way as has been experienced in other interactive communication structures, such as education and entertainment. For instance, consumers accord a higher value to interactive entertainment software than to passive software, due to the greater stimulation afforded by this mode. In entertainment software, an example would be some of the new video games that present a mode which runs like an animated cartoon until one elects to interact. As an animated cartoon, the video usually becomes boring within minutes. But as an interactive video game, the software stimulates the user with hours of entertainment.

In summary, a computerized interactive system increases the client's ability to resolve problems at the site where behavior occurs, and adjusts him within the framework of a preset goal. By including, within the context of the personalized message, challenges in the form of questions, an entertaining and stimulating process can be added due to the increased feedback or interactive nature of new telecommunication technology.

With regard to the prior art, many types of systems have been used in endeavoring to provide an effective means for providing surveillance over a behavioral modification client by using a telecommunication link. However, these prior art systems have not disclosed an adequate and cost-effective telecommunication network that uses a computer in combination with a telephone to provide positive motivational messages and/or questions that are answered by a client by means of a dual tone multifrequency telephone set.

Further, the prior art systems have not disclosed utilization with such hardware as voice stress analyzers, olfactory units, CD-ROM platforms, interactive television in connection with a telecommunication link as a further behavioral modification means in use with the client.

A search of the prior art discloses patents that show different types of feedback mechanisms:

| PATENT NO. | INVENTOR | ISSUED |
| --- | --- | --- |
| 3,742,938 | T. J. Stern | 3 July 1973 |
| 3,808,694 | W. Y. Hutchinson et al. | 7 May 1974 |
| 4,112,425 | G. J. Zobrist et al. | 5 September 1978 |
| 4,237,344 | Moore | 2 December 1980 |
| 4,328,494 | R. Goodall | 4 May 1982 |
| 4,377,214 | G. G. Hansen et al. | 22 March 1983 |
| 4,396,976 | G. P. Hyatt | 2 August 1983 |
| 4,602,127 | J. F. Neely et al. | 22 July 1986 |
| 4,773,492 | E. Ruzumna | 27 September 1988 |
| 4,831,242 | W. H. Englehardt et al. | 16 May 1989 |
| 4,835,372 | Gombrich et al. | 30 May 1989 |
| 4,916,435 | Fuller | 10 April 1990 |
| 4,922,514 | Bergeron et al. | 1 May 1990 |
| 4,912,552 | Allison III et al. | 27 March 1990 |
| 4,933,873 | Kaufman et al. | 12 June 1990 |
| 4,952,928 | G. T. Carroll et al. | 28 August 1990 |
| 5,008,835 | Jackmann et al. | 16 April 1991 |
| 5,014,298 | Katz | 7 May 1991 |
| 5,018,736 | Person et al. | 28 May 1991 |
| 5,023,901 | Sloan et al. | 11 June 1991 |
| 5,036,462 | Kaufman et al. | 30 July 1991 |
| 5,068,080 | Impink Jr. et al. | 26 November 1991 |
| 5,085,527 | P. A. Gilbert | 4 February 1992 |

The Sloan et al., patent discloses a surveillance system which integrates voice identification with passive monitoring mechanisms. The system comprises a central station located at a supervisory authority and a plurality of remote voice verification units. Each unit is located at a designated locality for an individual under surveillance and is connected to the central station via telephone lines. The central station consists of a control computer system and a violation computer system. The central station maintains and analyzes all relevant data for each individual, and initializes and retrieves information from each voice verification unit. Each voice verification unit conducts a voice verification test of a respective individual according to test schedules outlined by the central station. Test and monitoring results obtained during a defined surveillance period are transmitted to the central station on a periodic or exigent basis. Each remote station has a modem input, test means input connected to a microphone, and a third input to receive passive monitoring signals. The active and passive signals are analyzed according to an algorithm and command signals received from the central station. The test means also has an output to prod the individual to speak a preselected series of words. The test schedule in each remote is randomly created for each period and individual.

The Fuller patent discloses a remote confinement monitoring station and system with a central office that provides means for automatic selection of a specific confinee. The central office selects scheduled or semirandom monitoring calls, to avoid a high degree of predictability by the confinee, auto dialing means for transmission of a prerecorded or synthesized audio instruction message to the confinee, and recording of information received in response to the acts of the selected confinee preformed in response to the communicated message. The central office has a computer with a telephone line modem, a voice synthesizer, and other accessories in displays for automatic recording of data received including a visual camera image and breath analyzer results, and can include automatic image comparison and violation signal alarming.

The Moore patent discloses a rapid response hospital health care communications system. The system includes an auto dialer telephone system to allow patients to communicate from outside the hospital to receive advice and health care as indicated by the patient's medical profile. The communications system includes a health care console with an information storing computer connected through various communication paths to in-hospital patients, and by telephone means to out-of-hospital patient locations. Each out-of-hospital location includes a communication interface with a telephone, a console, and a hand-held remote control comprising a plurality of sensors, indicators and features. The interface includes an auto dialer and auto identifier that dials the health care console and identifies the patient by a computer recognizable code.

The Kaufman et al., patent discloses an interactive patient assisting device that has both preselected doses of medicine and a physical testing device that can communicate with a remote medical center over the telephone system. The system includes a clock/calendar unit that can be programmed to establish a schedule of a variety of activities, a pharmaceutical dispenser, a voice synthesizer and recognitions unit, a computer, displays, and monitor means for blood pressure, oxygen and temperature. For communicating to a remote location, an automatic dialer, modem and telephone are included.

The Bergeron et al., patent discloses a method and system for the dispatch of resources to remote sites in response to alarm signals. A processor accesses the database of, for instance, a field service engineer designated to provide services to particular remote sites in response to the alarm signals received from those sites. The processor then attempts to establish a telephone connection with the field service engineer and provide the engineer with information by means of synthesized voice messages. The system may execute remote diagnostic programs and determine the results and attempt to communicate with selected resources. The system has a conventional processor with a database, voice synthesizer, voice system and auto dialer. When the system dials and the telephone is answered, the system requests an identification code by means of the touchstone buttons before it communicates.

The Hutchinson patent discloses a weighing and height measuring device. It is especially adapted for use with a remote digital read-out system. The device comprises a weight responsive moving platform connected by cable to a remote digital read-out unit. One of the objects of the invention is to provide a weight measuring device adapted for use with a remote read-out and/or computer input device.

The Stern patent discloses a cardiac pacer and heart pulse monitor for remote diagnosis wherein information from a pair of sensors is transmitted by means of a telephone handset and transmitter, over a commercial telephone system to a remote receiver. Information received at the receiver may then be processed by means of an appropriate computer and program system.

The Carroll patent discloses an adaptable electronic monitoring system. The system is configured to fit the needs of a particular monitoring or identification application by selecting appropriate modules. The system provides for monitoring at a central location and communication between the location of the sensed information to the processing site by means of a normal telephone communications system.

The other cited patents are for background purposes and are indicative of the art to which the invention relates.

It will be noted that the above mechanisms and systems do not allow the utilization of various well known elements used in a unique random calling manner with a client database and client program of prescribed messages and/or questions for particular persons. More particularly, the instant apparatus and method provides a uniquely reinforcing approach of allowing the use of prescribed messages and/or questions for particular persons. More particularly, the instant apparatus and method provides a uniquely reinforcing approach of allowing the use of random calls at random locations from a list of possible locations where a client may be located. Furthermore, this system utilizes existing telephone technology unlike many of the devices described in the above referenced patents.

SUMMARY OF THE INVENTION

The automated and interactive positive motivational system is designed to be used by doctors, psychologists, counselors or other trainers to provide motivational messages and/or questions to clients having behavioral, weight, volitional or motivation problems. Its basic configuration comprises:

(a) means for recording and accessing a client's database that includes for each client the name, schedule of telephone numbers where the client may be reached during each 24-hour period, personal identification number, and previous history of messages and the client's responses;

(b) means for measuring and recording a client's weight without revealing their weight to them and transmitting said weight information telephonically for use in a weight reduction program;

(c) first means for recording and accessing a client's program that includes for each client specific motivational messages, personal and unique metaphoric references, and/or questions that are to be responded to by the client through either the telephone interactive beeper, personal communicator, or interactive television;

(d) a computer having means for accessing the client database and said client program. If a match is found between a client's database and client program, the computer produces a sequence, a digital telephone signal and corresponds to a client's telephone number or beeper or personal communicator number, a digital client validation request signal and a digital motivational message(s) and/or questions. The messages and/or questions are only then sent if the client's validation request signal is responded to by the client with a valid personal identification number (PIN) in the telephone mode, or broadcast without a PIN with a beeper or personal communicator;

(e) means for converting the digital signals produced by the computer to telephone tone signals that are sent to a client's dual tone multifrequency telephone set via a telephone network. The telephone set is used to respond to the client's validation request, hear the motivational message(s) and/or to respond to the questions;

(f) means for converting the telephone tone signals originating at the client's telephone set to digital signals for application to and processing by the computer; and (g) second means for permanently recording all the outgoing and incoming client communications.

An important object of the invention is that the system manipulates speech messages that are stored, not in an analog format common to audio tape storage systems, but in digital format that is stored on a read-only compact disc, a computer hard drive or the like. The use of compact discs allows the system to access files quickly and accurately. Therefore, it is possible for the computer to access more than one speech file at a time. Each telephone line that the system is servicing is actually a small "slice" of computer time during which speech files are being played from or recorded. The more lines that are active, the more slices of time that must be managed. The system provides the functions to operate with more than one telephone line simultaneously, thereby allowing a counselor, at all times over a 24-hour period, to process and supervise many more clients than otherwise. In addition, the system allows for a client to receive more doses of intervention over any time period than in any other manner.

Another object of the invention is directed to accomplishing most tasks in a voice response application by accepting, recognizing and making decisions based on a keypad input from the caller's dual tone multifrequency telephone. The keypad generally sends dual tone multifrequency (DTMF) tone signals but occasionally multifrequency (MF) tones are used by certain types of telephone switching equipment. While these two signalling methods are not compatible, the system will work with either one equally well.

Still another object of the invention is the use of digitized voice signals for the transmission of messages to the client. Digitized voice signals are typically made by sampling the voice wave form 6000 to 8000 times per second in order to accurately reconstruct good speech quality. Each sample takes 8 to 12 bits, this results in 48,000 to 96,000 bits of information per second that must be stored. It is common in telephonic applications for a digitized voice to be compressed by storing only the differences between samples. Therefore, the speech card that the system supports uses a compression technique known as Adaptive Differential Pulse Code Modulation (ADPCM) which recognizes that there is only a small difference between the speech samples and stores a logarithmic function of the difference between speech samples. The result is good speech quality at only 3000 bytes per second of data throughput.

Yet, another object of the invention is that the client program may be directed to any subject matter such as motivational training, teaching, psychological behavior modification, religious training, indoctrination and reinforcement by sales managers, psychologists, ministers, counselors, wherever motivations would be facilitated by daily or periodic intervention. The following is a partial list of some of the component areas that the client program may be directed to:

1. nutrition
2. creativity
3. exercise
4. weight loss (diet/weight management)
5. optimism (and hope)
6. life-long learning
7. time management
8. stress management
9. happiness (and purpose)
10. optimal health
11. relationships
12. thrift/financial freedom (reduction of consumption)
13. risk/courage
14. new, balanced image, enhanced self-esteem (beauty)
15. immune system enhancement
16. midlife transformation/emergence
17. women and men in aging and transition (heart disease, menopause, etc.)
18. control or self-discipline
19. intuition enhancement
20. high energy
21. spiritual insight Accordingly it is an object of the present invention to record the daily activity schedule of each client enabling contact with the client on a scheduled or random basis by telephone or by other means such as an alpha-numeric pager or modem that is used to contact clients wherever the client may be during the day or night. If the client misses a call, they may call in to the computer and get their message by using a specific password.

The rationale of the system is that man is in a continuous state of growth and development. The system provides the motivation through continuous daily monitoring of each client as he works towards their basic goals for optimal health, personal success, longevity and happiness. By this daily reinforcement and guidance utilizing stimulating feedback, the system is able to maintain the organization and intervention between the client and his goals.

These and other objects and advantages of the present invention will become apparent from the subsequent detailed description of the preferred embodiment and the appended claims taken in conjunction with the accompanying drawings.

BRIEF DESCRIPTION OF THE DRAWINGS

FIG. 2B is a continuation of the application of FIG. 2A.

DESCRIPTION OF THE PREFERRED EMBODIMENT

Figure 1:
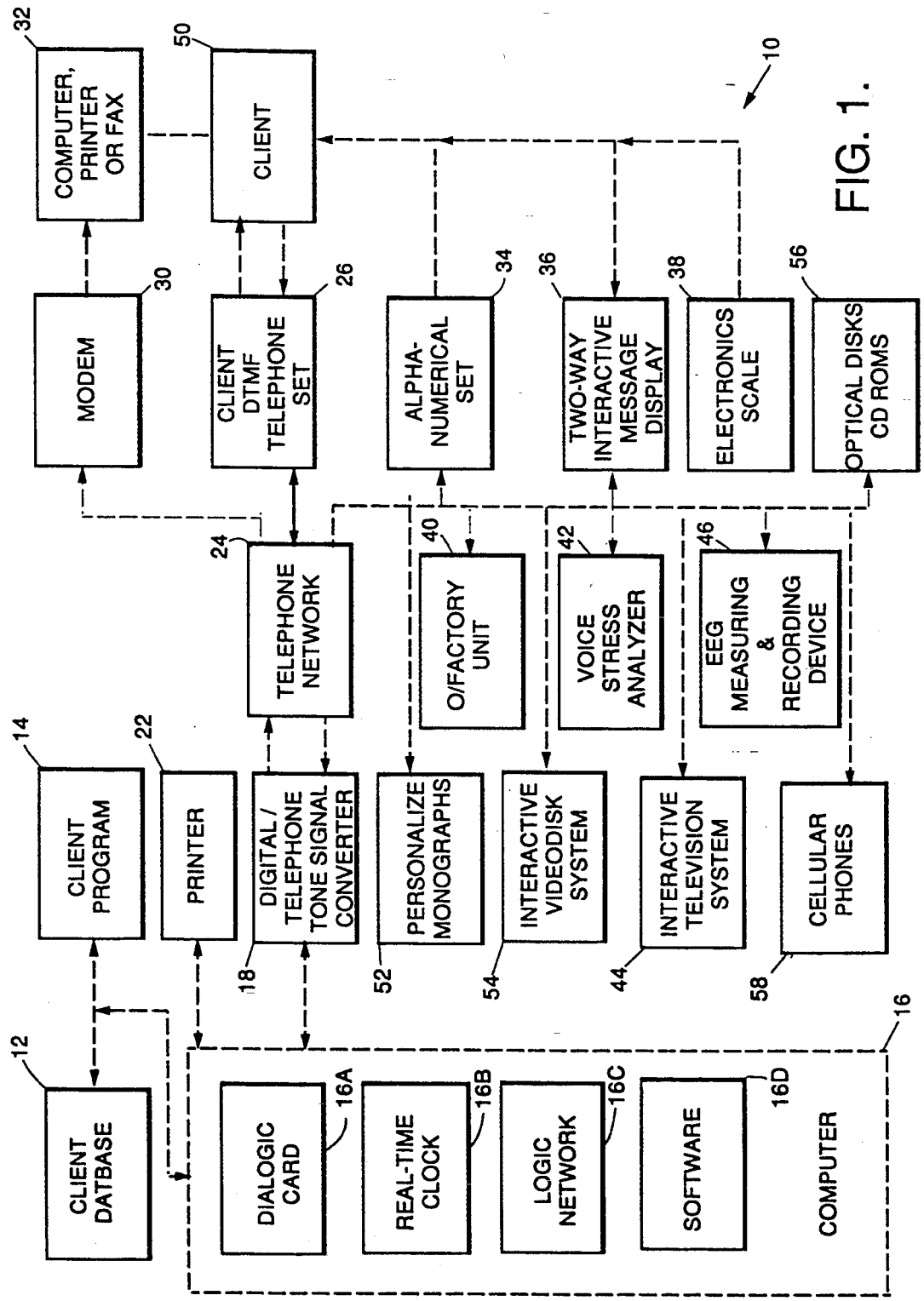
FIG. 1 is a block diagram showing the interactive activity between the system and a client of the present inventor.

The best mode for carrying out the invention is presented in terms of a preferred embodiment that is designed to allow doctors, psychologists, counselors and other trainers to maintain surveillance over their clients by utilizing a telecommunication link to perform automated information exchange. The preferred embodiment of the automated and interactive positive motivation system 10, as shown in FIG. 1, comprises a means for recording and accessing a client's database 12 and a client's program 14, by using a computer 16, having a digital signal/telephone tone converter 18 and a printer 22, wherein access means comprise a telephone network 24 and a client dual tone multifrequency telephone set 26. A client 50 uses the system 10 which can also be enhanced by the incorporation of the following elements that are operated by the telephone network 26: a modem 30 that operates a computer printer of facsimile machine 32, an alpha-numeric pager 34, a two-way interactive message display 36, an electronics scale 38, an olfactory unit 40, a voice stress analyzer 42, an interactive television system 44, an EEG measuring and recording device 46, personalized monographs, interactive video, optical discs, i.e., CD-ROMs, and cellular phones.

The client database 12 in the preferred embodiment consists of a compact disc (CD) recording that is played back on a CD player that interfaces with the computer 16 as shown in FIG. 1. However, other database recording and playback units can also be used. These units include but are not limited to a tape cartridge that is played back to the computer by means of a tape cartridge player or an optical disc and optical disc playback unit. The client database includes for each client 50, the client's name, their calling schedule by week, day and time, each client's personal identification number (PIN), and previous history of messages.

The client program 14 in the preferred embodiment, is also recorded and played back by a CD player or other recording and playback units, as described above for the client database 12, and is connected to the computer and to the telephone network 24 as shown in FIG. 1. The client program 14 is especially designed to serve a plurality of specific clients. The program 14 can include as many motivational and reinforcement messages as are necessary to help with a specific behavioral problem. The motivational and reinforcement messages are designed to provide therapeutic intervention at specific or random times and more particularly to provide therapeutic intervention at the site where the behavior to be corrected occurs. In the field of behavioral reinforcement it has been found that even with the best of intentions, relapses usually occur within several days following the reading of a book or attending a seminar to several months after the conclusion of a behavioral modification program. Thus, by transmitting behavioral motivation and reinforcement messages on a periodic or random basis, the behavioral modification program can continue on course to a curable conclusion.

In addition to or in combination with the messages, the system 10 is also designed to send a client behavioral modification questions. These questions are answered by the client by pressing on a specific key on the keypad of the dual tone multifrequency telephone set 26. The answers to the questions are analyzed by the client's doctor or trainer to find root problems and to determine the next series of messages and/or questions that are to be transmitted to the client 50 at the next transmittal period. All messages, questions and the client's response to the questions as well as the time, date, duration of each call and touch tones entered by the client 50 are retained in a permanent log or record by means of the printer 22 which is directly connected to the computer 16 as shown in FIG. 1.

The telephone by its very nature, has always been interactive on a two-way basis and because of its wide usage it lies within the comfort zone by nearly all clients. The telephone is also cost effective and is convenient for both the caller and the client. Additionally, social learning theories suggest that education carried out in the setting in which the behavior is taking place will have the greatest impact. Thus, telephone counseling at home or in the work place may have greater behavioral impact than direct clinic. For clients who cannot come to a clinic because of their physical condition, distance or the presence of a psychiatric disorder that makes the intimacy of face-to-face contact intolerable, the telephone is the sole means for counseling. By calling clients on their transportable or cellular telephones 58, behavioral reinforcement can also be provided for clients on the go and increase the instances wherein motivation can be provided in the place where the behavior occurs.

The client database 12 and client program 14 interface with the computer 16 that in the preferred embodiment consists of an IBM-AT compatible computer 16 having at least an 80386 coprocessor. The client database 12 and client program 14 as described above, are externally stored as shown in FIG. 1. However, these elements may also be stored on a hard disc located within the computer 16 or on other mass media storage devices such as CD-ROM or removable mass media cartridges. The computer 16 is configured in part to include a Dialogic D41 4-line speech card 16A, having a real-time clock 16B and a logic network 16C, operated by the system software 16D.

The Dialogic card 16A allows a speech compression technique to be used that samples a small difference between speech samples and stores a logarithmic function of the difference between the speech samples. This technique results in good speech quality at only 3000 bytes per second. The real-time clock 16B sets and selects the appropriate time for a particular client to be accessed from the client database 12 and the client program 14. The logic network 16C provides the logic necessary to determine if a match between the client stored in the database 12 and in the client program 14 is available. The system software 16D provides the algorithms to operate the system 10 in combination with the logic network 16C. The operating steps of the software program are shown in the software flowchart included as FIG. 2 and listed in source code format in Appendix 1.

Figure 2A:
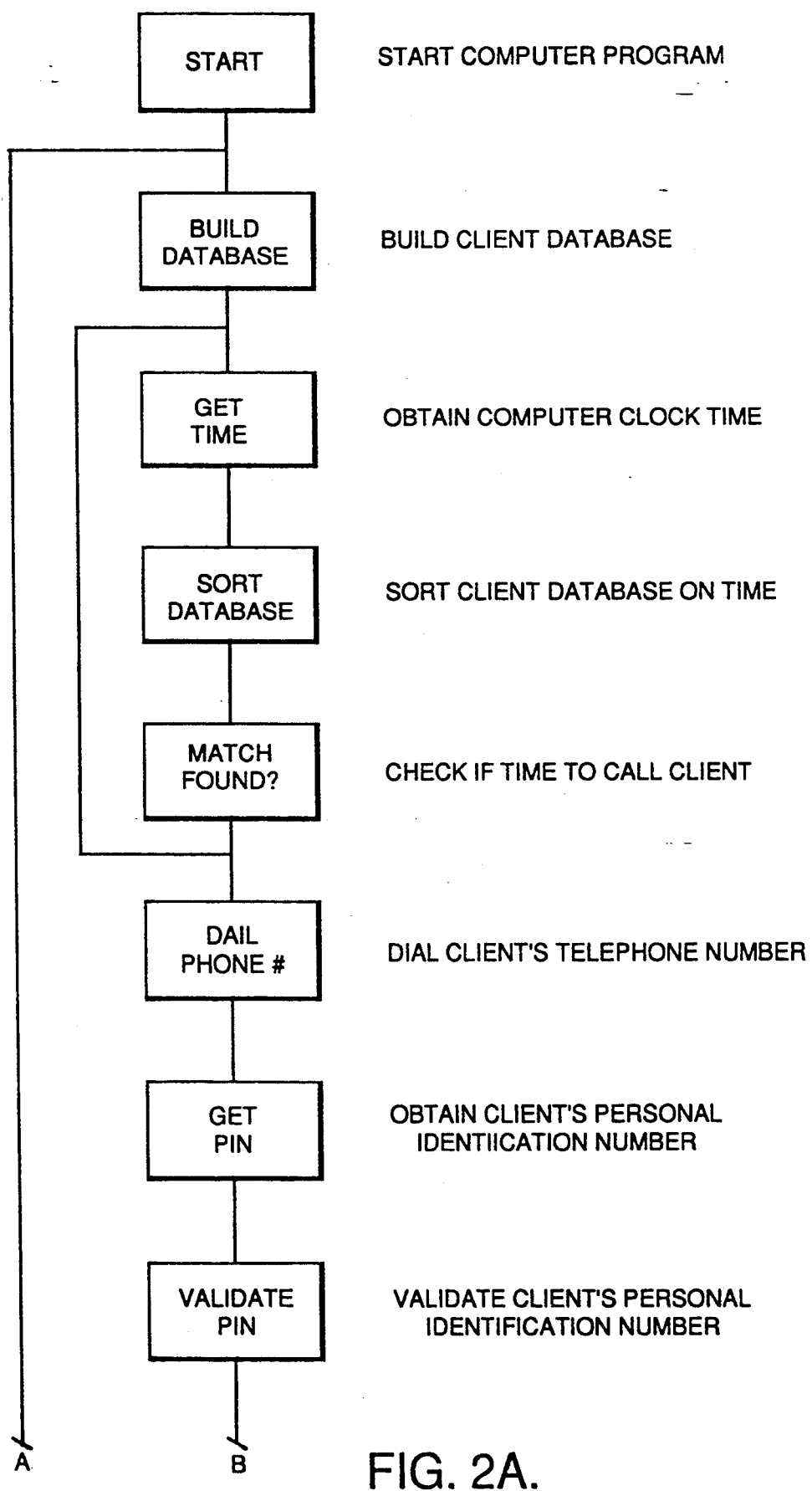
FIG. 2A is an application flowchart of the computer software used in FIG. 1.

As shown in FIG. 2, the computer program builds a client database and sets the database to a computer clock time. In a typical operating sequence, the computer 16 at a preselected week and time, accesses the client database 12 and the client program 14. If a match is found between the client's database 12 and program 14, the computer 16 via the logic network 16C, produces in sequence, a digital telephone number and a digital client validation request signal.

Both of these signals are applied to the digital signal/telephone tone signal converter 18. The converter 18 includes circuit means to accept and convert the digital signals from the computer 16 to telephone tone signals that correspond to the client's telephone number and a personal identification number. The converter 18 can also be designed to include a telephone number redial circuit and a random telephone number dialer circuit. The redial circuit allows a client's busy telephone number to be automatically re-dialed at selectable time intervals. The random number dialer allows client telephone numbers stored in the client database 12 to be randomly selected and called.

From the digital signal/telephone tone signal converter 18, the telephone tone signals are applied as shown in FIG. 1 to a telephone network 24. The network 24 relays the tone signals to the client's dual tone multifrequency telephone set 26 from where the client 50 can answer the telephone 26 and respond to the request to provide a personal identification number. The client 50 responds by pressing on specific keys on the keypad of the telephone set 26. If the client 50 responds with a valid number it is routed via the telephone network 24, back through the converter 18 to the logic network 16C in the computer 16. Upon the receipt of a valid number, the logic network 16C enables the client program 14 to allow the audio signals carrying the messages and/or questions to be transmitted via the telephone network 24 to the client's telephone 26 from where the client 50 can receive the message and respond to the questions.

The telephone network 24 used in the preferred embodiment is serviced by the local telephone public utility company. However, if a closed circuit operation is desired, such as within the confines of an enclosed area or building, a private telephone network may be employed. In either of the above scenarios the clients dual tone multifrequency telephone set 26 may be hardwired to the telephone network 24 or, a transportable cellular 58 that uses RF or satellite communication links may be used. By calling a client 50 on their transportable cellular telephone 58, the motivation message can in many instances be sent to the place when the behavior is occurring when the message carries its greatest effect. As also shown in FIG. 1 by dotted lines, in lieu of making the initial client contact by using the telephone set 26, the contact can be made by means of a modem 30, an alpha-numeric pager 34, a two-way, interactive, computer activated message display 36 or other such devices. If a modem 30 is used, it can be connected directly to a computer printer or facsimile machine (FAX) 32. In this client alerting medium, after the client 50 receives a motivational message or a question, the client 50 response can be made by calling the computer 16 on the dual tone multifrequency telephone 26 by use of a special computer access telephone number. Likewise, if an alpha-numeric pager 34 is used the client response would be made as previously described. The use of a two-way interactive message display 36 further provides an enhanced client interface in that graphics can be included with the messages and questions. The display 36 is connected directly to the computer 16 via the telephone network 24 and digital/telephone tone signal converter 18. Likewise, an interactive television system 44 can be used wherein customized broadcasts can be responded to by individual clients or whole classes of subscribers, providing a low cost alternative to individual customized instruction. In addition to or in lieu of an interactive television system 44, an interactive videodisc system 54 comprising a videodisc player and monitor interfaced with a microcomputer may be used.

With the use of optical discs or CD-ROMs 56, a computer-based information metering system is envisioned wherein a client 50 will be billed through the use of an encryption-metering device only for amount of therapy the client 50 wishes to access.

The motivation and behavioral messages and client questions can also be used in combination with auxiliary devices to fortify the client's messages or questions. For example, in the field of weight loss, an electronics scale 38 can be utilized to supply the timely weight of the client to determine if a weight loss or gain has occurred during the reporting period. As shown in FIG. 1, the electronic weight scale is connected to an ordinary telephone line which automatically dials the telephone number associated with the operating system and transmits the weight of a client 50 standing on the scale 38 digitally to the client's program 14 and database 12 for later analysis in accordance with a weight reduction program.

The scale 38 prevents the client 50 from becoming aware of their day-to-day weight fluctuations. This is consistent with new insights in behavior theory with respect to human motivation which allow an observer or instructor using the computer to review the client's weight periodically through the use of the computer 16 which is at a remote location and can guide the client 50 from time to time based upon the trend or average of their weight, and other devices such as glucose monitoring, blood pressure, heart rate, and cholesterol monitoring.

Research reported by Mori and Morey in 1991 shows that individuals with depression or lower levels of self-esteem are more likely to have a vulnerable or negatively distorted body image (The vulnerable body image of females with feelings of depression, *Journal of Research in Personality*, Vol. 25, 343-354). Furthermore, Nelson and Craighead's 1977 study (Selective recall of positive and negative feedback, self-control behaviors, and depression, *Journal of Abnormal Psychology*, Vol. 86, 379-388), suggests that depressives distort environmental input in such a way that they consistently reach a negative conclusion. Since the depressed person "filters out" a certain amount of positive feedback and is particularly sensitive to negative feedback, it is important to control or limit the frequency of negative feedback (i.e., weight readings).

The scale 38 does not have any visible measurement display on its exterior and may be fabricated in the shape of a flat mat by use of strain gauge technology or the like for placement in various rooms within a client's dwelling. While not shown in the drawings, it may be envisioned that the scale 38 may be placed in front of a refrigerator door wherein the clients weight is measured at a period of time before the client intakes food.

Another preferred embodiment, shown in FIG. 1, is the use of an olfactory unit 40 which provides a variety of different smells to the client 50 to be used in memory association with the daily telephone interaction. Researchers have successfully trained animals to recognize several different scents and to behave in particular ways when they did—for instance, to lick or chew in expectation of food or water as reported by W. J. Freeman, The physiology of perception, *Scientific American*, 78-85 (February, 1991). A more recent study entitled Olfactory stimuli as context cues in human memory, by A. Cann and D. A. Ross and reported in *American Journal of Psychology*, 91-102 (1989), indicates that an olfactory context cue, when paired with a learning experience, might later be used to produce more efficient performance of the learned behaviors. In fact, the client 50 could carry the proper olfactory stimulus 40 for release at the critical time when performance is finished, thus enhancing the motivational training by providing accessing cues in a way not previously taught in the prior art.

A 1990 study by Frank R. Schab at Yale University ("Odors and the remembrance of things past" reported in *Journal of Psychology: Learning, Memory and Cognition*, Vol. 16, 648-655), further builds upon the evidence that odors can effectively be used as memory retrieval cues to enhance learning and performance. This is consistent with the "encoding specificity hypothesis" of Tulving & Thompson ("Encoding specificity and retrieval processes in episodic memory,"*Psychological Review*, Vol. 80, 352-372 (1973), which states that contextual stimuli (i.e., olfactory cues) are encoded along with target information on learning and serve as memory cues to the target information at retrieval.

Yet another preferred embodiment shown in FIG. 1 incorporates the use of a voice stress analyzer 42, which offers a digital numerical evaluation of the speaker's voice stress level to monitor a client's response during a behavioral motivation reinforcement question. Research by D. O'Hair and M. J. Cody entitled "Gender and vocal stress differences during truthful and deception information sequences," in *Human Relations*, Vol 40, 1-14 (1987), indicates that voice stress analyzers can be objectively and unobtrusively used to detect vocal stress indicative of deception. If a client 50 knows that his veracity is being tested and that his responses are being analyzed for deception, then there is greater motivation on his part to adhere to the program 14 and hence more rapidly progress towards a particular goal. In addition, commonly encountered self-deception is reduced using this mode.

Another preferred embodiment incorporates the use of an EEG measuring and recording device 46 which can be used to assess hypnotic susceptibility either in the presence of the client 50 or at some distance by use of a modem for transmitting signals which indicate various brainwave states. Behavior research indicates that there is an increase in alpha activity in the EEG when subjects are exposed to behavioral intervention techniques such as hypnosis, relaxation and meditation. In addition, studies with psychotropic drugs have demonstrated that increased and synchronized alpha activity is a characteristic of all the major tranquilizers. A 1972 study by G. A. Ulett, S. Akpinar and T. M. Itil ("Quantative EEG analysis during hypnosis," *Electroencephalography and Clinical Neurophysiology*, Vol. 33,361-368) reported significant EEG differences between the hypnotic and awake states, with all subjects experiencing increased alpha activity in the hypnotic state. The computer 16 in this mode, receiving and analyzing the signals, can then adjust the intervention to correspond to the client's 50 brainwave state.

Another preferred embodiment shown in FIG. 1, is a computer-driven system for motivational reinforcement and guidance which can be applied to various modes of interactive television 44. Its feature of providing customized instruction, learning, and motivational prompts and cues, often where the behavior occurs, provides a unique approach toward directed interactive learning and behavior modification. Using interactive television 44, the computer-driven system converts the traditional broadcast format to a customized "narrowcast," where either classes of learners or individual subscribers are addressed according to their individual issues without specific categories, and each in turn returns individual specific responses to questions or polling, which are then recorded in the client database 12. This application becomes possible because of the larger number of channels available with fiber optic cable facilitating two-way interaction.

It is envisioned that three separate modes of transmission from a computer can be utilized:

(1) fiber optic cable for two-way communication—the computer transmission would appear on the subscriber's screen and he would in turn reply either through a remote control unit or telephone back over the fiber optic cable. The computer would receive his return transmission or reply and note it accordingly in its memory. Periodic and finer tuned follow-up reinforcement could occur via telephone based upon the client's responses over specific time periods.

(2) coaxial cable—inasmuch as existing coaxial cable systems can transmit hundreds of times more data than a conventional telephone line, the subject computer driven system can transmit learning, motivational guidance and reinforcement to classes of subscribers over existing coaxial cable systems and the subscribers can reply using a remote unit containing computer hardware for reply back over the cable. Alternatively, the remote unit can contain a modem for reply back over a telephone line.

(3) wireless cable—subscribers without cable would receive the signal via antenna in the case of localized transmission or dish in the case of satellite transmission. The transmission would contain the computer driven learning, motivation and reinforcement. The subscriber would reply via telephone.

In each mode of transmission, subscribers can be reminded of an upcoming transmission via telephone 26 or wireless radio beeper 34 as described herein. Additionally, explanatory brochures can be used with any of the above described interaction as a method of further reinforcing a client 50 toward a particular goal. With today's technology and regulatory infrastructure, programming for interactive television would remain in its current analog form and a special unit, usually a controller box plus remote positioned atop the TV set, would allow the viewer to dip into the data stream and manipulate what appears on the TV screen. With digital and compression technology (compression six or more digital channels into the same bandwidth as one analog channel), a settop box would be used to decode and decompress video and audio signals in real time.

Another preferred embodiment is the use of a computer-based information metering system that uses optical discs 56 as transport and storage media, encrypting to protect data and metering to permit usage by clients on a pay-per-view or pay per bit of information basis. The encryption-metering device would use digital technology and would be made available through cellular phones, wireless cable transmission, interactive television and CD-ROM. Information would be distributed in encrypted form to users. After the user browses through the menu or index at no charge and selects the item needed, the encryption-metering device will decrypt the information required, record which data was used, by whom and for what issues or subjects, and will permit the user to be billed only for the data used. This information would be unreadable or unlistenable until decrypted and users would be charged based on the number of bits of information selected. A metering chip or computer board would be used to gauge data use just as an electric meter tracks power demand. Information may be retrieved in either full-text audio or image form. A decryption program keeps track of how much data is decoded and can subtract its costs from a prepaid credit stored on a chip as a form of payment. The encryption-metering technology may use a Microsoft Windows ® based application, with familiar graphical interfaces and menuing systems to which users are accustomed, and would be available on a variety of computer platforms.

Another preferred embodiment is the use of CD-ROM 56 (Compact Disc with Read Only Memory), a high-density storage and delivery medium similar to digital audio compact discs, which stores vast amounts of data in a digital form. Each CD-ROM 56 will hold about 600 megabytes of data, equivalent to a shelf of books almost 100 feet long, with a full text index. CD-ROMs 56 offer the fastest and most convenient way to access material from large data bases. However, most present CD-ROM systems require the user to purchase an entire data base on CD-ROMs. By contrast, the use of encryption technology and metering allows the applicant to distribute each CD-ROM for little or no cost and then charge the user only for the information actually used. The CD-ROMs 56 would be used with standard as well as portable CD-ROM players, allowing users instant access to the material virtually anywhere.

Still another preferred embodiment shown in FIG. 1, is the use of monographs or "bibliotherapy" 52 as an adjunct to audio, video and in-person feedback. In a study of women in a weight reduction program, the use of written handouts was found to improve levels of self-esteem, assertiveness, attitudes to body size, and self efficacy about weight control. (A. J. Blair, V. J. Lewis, and D. A. Booth, "Response to leaflets about eating and shape by women concerned about their weight," *Behavioural Psychotherapy*, Vol 20, . 279–296 (1992) ) .

Another preferred embodiment is the use of interactive video system 54 to accelerate the learning process. An interactive videodisc 54 system implies that a videodisc player and monitor are interfaced with a microcomputer, thus allowing control of the progression of the program 14. Prior art systems have decreasing capabilities essentially consistent with reduced computer memory. These prior art systems allow proportionally less user control and interactivity. Research shows that with interactive video systems 54, effective learning tends to occur in one-third to one-half of the time required for the same content presented through more traditional approaches (G. Kearsley and J. Frost, March, 1985, "Design factors for successful videodisc-based instruction; *Educational Technology*, 7–13). Positive student responses to the use of interactive video technology (IVT) are reported in the literature (L. Jones and S. G. Smith, March, 1989, "Lights, camera, reaction! The interactive videodisc: A tool for teaching chemistry," *T.H.E. Journal*, 16(7), 78–85) and IVT appears to be particularly well-suited for learning and behavior modification: learning occurs in an environment free from observation and evaluation, users have the freedom to err and to observe the consequences of their decisions, and to use problem-solving strategies to bring about corrected action. Dr. Marion Diamond, at University of California Berkeley, has reported, based on extensive experimentation on rats, that the structure and abilities of the cerebral cortex can be changed throughout life by enriching sensory environments; she concludes that we can actually become smarter as we grow older if we provide our brains with the right encouragement and environment. Indeed, newer learning theories and recent brain research emphasize the importance of an active, empowered learner participating and interacting fully in the creation of his or her own learning.

Although not shown it may be envisioned that another preferred embodiment is the application of the spiral or staged model of change in a multifaceted behavioral modification program. Researchers James Prochaska, Carlo DiClemente and John Norcross have created a spiral model of change which conceptualizes the process of change in a non-linear framework. Their research revealed that relapse is the rule rather than the exception among individuals with addictive behavior patterns. Therefore, by reframing relapse as a normal stage in the process, their model suggests that relapse is merely a temporary setback and that most relapsers do not regress all the way back to where they began. Instead, they use relapse as a learning experience from which to attain newer heights and move forward, in a spiral process change. The spiral model of change depicts the cycle of change as consisting of 5 or more distinct stages. Prochaska, et al., have found that each of these stages is characterized by a set of specific behavior patterns. The likelihood of successful change appears to be directly linked to an individual's position on the spiral (i.e., the particular stage within the model). Indeed, the progress made by patients as a result of professional interventions tends to be a function of the stage they are in at the start of treatment.

By integrating the processes and stages of change as outlined by Prochaska et al., to create a multifaceted and multidimensional treatment system, this system tailors particular behavioral interventions accompanied by facts of the subject invention and its embodiments to clients in a customized manner consistent with the location they are in within each cycle and stage within the aforesaid spiral process. For example, during the contemplation stage, individuals are most open to consciousness-raising techniques and are more likely to use bibliotherapy and other feedback and reinforcement educational techniques. During the "action stage," clients need help with behavioral processes such as counter-conditioning and stimulus control to prevent relapse. And, during the "maintenance stage," there is a continued emphasis on coping skills as well as a focus on improving self-efficacy levels. In some cases, the same intervention or technique may be used across several different stages of change, but with varying degrees of intensity and/or frequency. There are numerous research studies which support the notion that matching therapy programs and processes to the client's stage of change, as conceptualized by Prochaska et al., will better serve the majority of clients.

An online and/or CD-ROM multimedia or video game with an ascending spiral interaction or script would be used as part of the program 14. Clients 50 would be consciously or unconsciously imprinting the spiral image in their minds each time they played the game, acting out or visualizing the process of contemplation, action, maintenance and relapse, and then starting again over the same cycle, thereby providing themselves with a strong sense of dramatic victory without personal or physical danger. The lessons learned, such as problem solving, pattern recognition, quick thinking, resource management and reasoned judgment, could then be gradually adopted with the client's life. For online users it may be envisioned that a settop box would be used to render interactive 3D graphics in real time.

Additionally, the use, separately or in combination, of multiple media such as audio, motion video, still images, graphics, animation, and text may be used to enhance the ability of the user to absorb and learn new information and make corresponding behavioral modifications.

It is also envisioned that the above described devices may be used in conjunction with personalized monographs 52 by one-on-one interviews to develop a client database to improve and enhance the audio, video and in-person aforementioned behavior modification techniques.

While the invention has been described in complete detail and pictorially shown in the accompanying drawings it is not to be limited to such details, since many changes and modifications may be made in the invention without departing from the spirit and scope thereof. For example, a variety of emerging telecommunication technologies provide varied platforms to transmit behavioral motivation and reinforcement. Some of these devices include: enhanced telephones containing LCD display screens for the representation of data and graphs; personal communication networks which use low power digital radio; palm-top calculators which received satellite transmissions as part of a nationwide network; wireless radio networks which exchange data on a national basis; digital cellular phones which signal their whereabouts on a continuous basis in order that their owner may be located anywhere in the world through linage to a satellite network; and personal digital assistants (PDA) which can receive data, organize it, monitor the client's activities, give reminders and then communicate via an internal modem as to the client's compliance with a central mainframe computer. Also, the application of the spiral or staged model of change may be applied to all of the behavioral modification programs heretofore discussed. Hence, the invention is described to cover any and all modifications and from which may come within the language and scope of the appended claims.

APPENDIX I

INTERACTIVE VOICE RESPONSE SYSTEM

IVRS ver. 2.0

GOIVRS. BAT
0.00
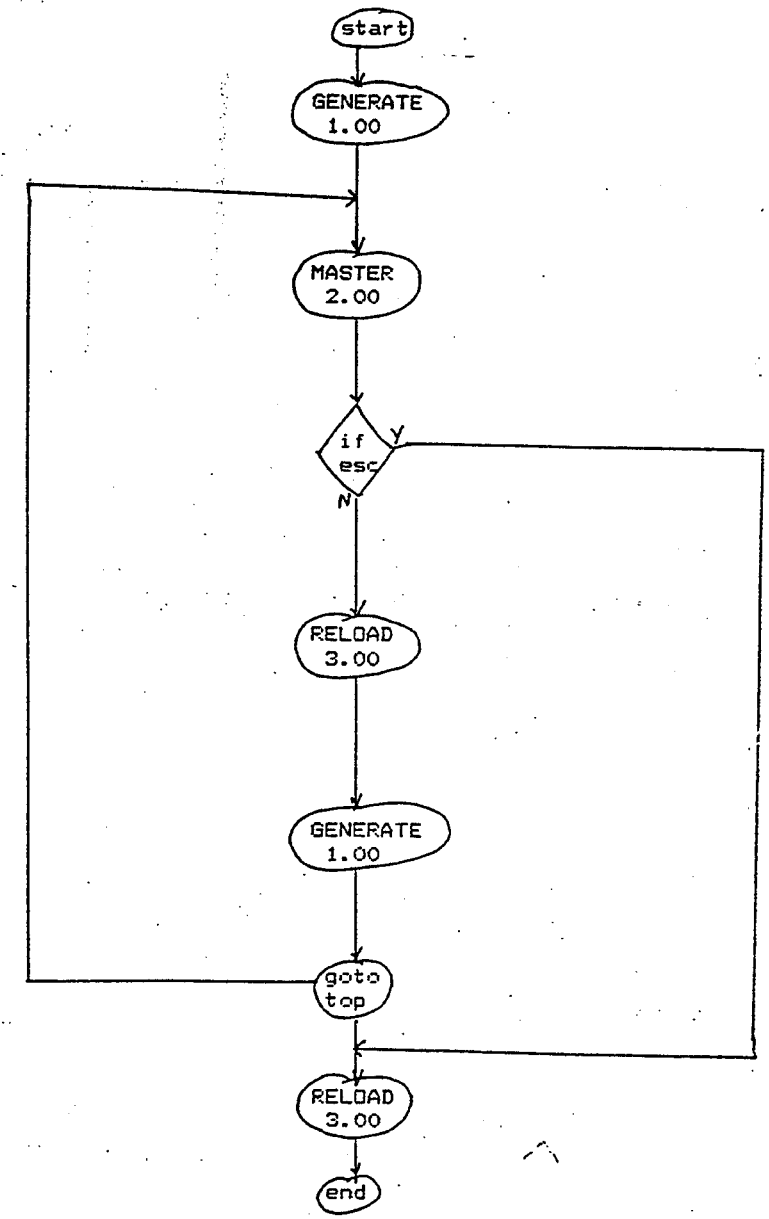
GOIVRS. BAT
```
btrieve /m:25/b:16/p:2048/f:25/c:/t:\btrieve.trn /e
GENERATE /A
butil -stop
:TOP
btrieve /m:25/b:16/p:2048/f:25/c:/t:\btrieve.trn /e
mark
btr
vos master
if errorlevel 123 goto GENERATE
goto end
```

```
:GENERATE
release
RELOAD /A
GENERATE /A
butil -stop goto TOP

:END
release
RELOAD /A
butil -stop
```

GOIVRS. (0.00)
This module is a batch file (.BAT) and is to be executed from the DOS prompt. This module contains three main routine GENERATE, MASTER and RELOAD.

Requirements: Before this module is run the Dialogic boards must be activated.
There must be at least one active phone line.

WATCHDOG (2.01)
This module checks if its time to make a call. If so, this module calls the outgoing subroutine.

INCOMING (2.02)
This module handles incomming calls, it loads the Btrieve templates and answers and hangs up when finished with the caller

OUTGOING (2.03)
This module controls outgoing calls, it loads the Btrieve templates, calls out and hangs up when finished with the caller.

GENERATE (1.00)
This module generates the call assignments for outgoing and incoming calls.

COPYRIGHT (1.01)
This module embeds the copyright agreement into the executable code

INITIALIZE_VARIABLES (1.02)
This module intializes the constants, variable type and pointers used throughout the GENERATE subroutines.

INITIALIZE_WINDOW (1.03)
This module intializes the window parameters for window shadows, exploding window, and window size.

INITIALIZE_ERROR_SCREEN (1.04)
This module initializes the error screen.

WRITE_ERROR (1.05)
This module writes error messages to the error screen.

DISPLAY_ERRORS (1.06)
This module displays the error screen.

EXIT_ROUTINES (1.07)
This routine closes the opened windows, return the user to the original directory and terminates the program.

LOAD_PLACEMENT_CODES (1.08)
This module loads the placement code from the Btrieve data base into memory.

OPEN_FILES (1.09)
This module opens the Btrieve data bases.

GENERATE_CALLS (1.10)
This module set the callers time slot and then creates and loads a call record.

CLOSE_FILES (1.11)
This module writes the control file then it closes all Btrieve files that were opened.

CLOSE_SCREEN_ERROR (1.071)
This module set the error screen pointers to a done state.

CLOSE_WINDOWS (1.072)
Thios module closes the windows that were opened and initailizes the screen CHECK_BTRIVE_STATUS (1.1081)
This modules checks the return status of the Btrieve data base.

GENERATE.PAS

```pascal
{$N+} program Generate_Call_Files;

{ Copyright 1992 PC Power Programs }

{DSV1.0-PROGRAM**********************************************
 *                                                              *
 * AUTHORS         : J. HARPER GAUSHELL                          *
 *                                                              *
 * SYSTEM          : TURBO PASCAL Version 5.5                    *
 *                                                              *
 * DATES           :                                             *
 *                                                              *
 * ENVIRONMENTS    :                                             *
 *                                                              *
 * OBJECTIVES      :                                             *
 *                                                              *
 * NOTES           :                                             *
 *                                                              *
 * MAINTANENCE     :    ---when---    ----who----    ---------what---------  *
 ****************************************************************} uses
  dos,
  clp2,
  Btrieve,
  OpDate,
  OpString,
  OpRoot,
  OpCrt,
  OpColor,
  IVRSColr,
  OpFrame,
  OpWindow;

const
  CallerInformationFile       = 'IVFIL002.DAT';   { Caller Information file }
  CallerTimeSlotFile          = 'IVFIL004.DAT';   { Caller Time Slot file }
  CallerMessageConstantsFile  = 'IVFIL006.DAT';   { Caller Message Constants file }
  CallerMessageInclusionsFile = 'IVFIL007.DAT';   { Caller Message Inclusions file }
  MessageCatagoriesFile       = 'IVFIL008.DAT';   { Message Catagories file }
  MessageInformationFile      = 'IVFIL010.DAT';   { Message Information file }
  PlacementCodesFile          = 'IVFIL012.DAT';   { Placement Codes file }
  LogCallFile                 = 'IVFIL013.DAT';   { Log Call file }
  LogMessageFile              = 'IVFIL014.DAT';   { Log Message file }
  ControlFile                 = 'CONTROL.FIL';    { Control file }

ProcessCodeIncomingCalls    = ' ';
  ProcessCodeOutgoingCalls    = 'C';
```

```
PlacementCodePrefixBeginning = 'B ';
PlacementCodePrefixEnding    = 'E ';

type
  CatagoryType    = array [1..20] of char;
  MessageIDType   = array [1..16] of char;
  PhoneNumberType = array [1..30] of char;

CallerInformationFileDef = record
                    IDNumber   : longint;
                    PassCode   : longint;
                    FirstName  : array [1..15] of char;
                    MiddleName : array [1..15] of char;
                    LastName   : array [1..15] of char;
                    Address1   : array [1..40] of char;
                    Address2   : array [1..40] of char;
                    City       : array [1..30] of char;
                    State      : array [1..2] of char;
                    ZipCode    : array [1..9] of char;
                    NoteLength : word;
                    Notes      : array [1..200] of char;
                  end;

CallerTimeSlotFileDef = record
              IDNumber      : longint;
              Day           : array [1..3] of char;
              BeginningTime : longint;
              EndingTime    : longint;
              PhoneNumber   : PhoneNumberType;
            end;

CallerMessageFileDef = record
              ProcessCode         : char;
              IDNumber            : longint;
              PlacementCodePrefix : array [1..3] of char;
              PlacementCodeNum    : word;
              MessageID           : MessageIDType;
            end;

CallerMessageFileDefPointer = ^CallerMessageFileDef;

MessageCatagoriesFileDef = record
              Catagory            : CatagoryType;
              CatagoryDirectoryNum : longint;
              DescriptionLength   : word;
              Description         : array [1..40] of char;
            end;

MessageInformationFileDef = record
              Catagory            : CatagoryType;
              Level               : longint;
              SubLevel            : longint;
              FileNumber          : longint;
              MessageID           : MessageIDType;
              AnnounceOnly        : boolean;
              ResponseLength      : integer;
              PlacementCodePrefix : array [1..3] of char;
              PlacementCodeNum    : integer;
              NoteLength          : word;
              Notes               : array [1..200] of char;
            end;

PlacementCodesFileDef = record
              PlacementCodePrefix : array [1..3] of char;
              PlacementCodeNum    : word;
              DescriptionLength   : word;
              Description         : array [1..200] of char;
            end;
```

```
LogCallFileDef = record
            CallNumber          : longint;
            ProcessCode         : char;
            IDNumber            : longint;
            PrimaryPhoneNumber  : PhoneNumberType;
            CallDate            : array [1..6] of char;
            CallTime            : array [1..6] of char;
            CallDuration        : longint;
            CallStatus          : array [1..15] of char;
            CallAttempts        : integer;
          end;

LogMessageFileDef = record
            CallNumber          : longint;
            SequenceNumber      : longint;
            ProcessCode         : char;
            MessageID           : MessageIDType;
            CompleteMessageID1  : longint;
            CompleteMessageID2  : longint;
            CompleteMessageID3  : longint;
            CompleteMessageID4  : longint;
            Response            : array [1..5] of char;
            ResponseLength      : integer;
            ValidResponse       : array [1..16] of char;
          end;

var
  CallerInformationBuffer                   : CallerInformationFileDef;
  CallerInformationBufferPointer            : pointer;
  CallerInformationBufferLength             : integer;
  CallerInformationHandle                   : byte;

CallerTimeSlotBuffer                      : CallerTimeSlotFileDef;
  CallerTimeSlotBufferPointer               : pointer;
  CallerTimeSlotBufferLength                : integer;
  CallerTimeSlotHandle                      : byte;

CallerMessageConstantsBuffer              : CallerMessageFileDef;
  CallerMessageConstantsBufferPointer       : pointer;
  CallerMessageConstantsBufferLength        : integer;
  CallerMessageConstantsHandle              : byte;

CallerMessageInclusionsBuffer             : CallerMessageFileDef;
  CallerMessageInclusionsBufferPointer      : pointer;
  CallerMessageInclusionsBufferLength       : integer;
  CallerMessageInclusionsHandle             : byte;

MessageCatagoriesBuffer                   : MessageCatagoriesFileDef;
  MessageCatagoriesBufferPointer            : pointer;
  MessageCatagoriesBufferLength             : integer;
  MessageCatagoriesHandle                   : byte;

MessageInformationBuffer                  : MessageInformationFileDef;
  MessageInformationBufferPointer           : pointer;
  MessageInformationBufferLength            : integer;
  MessageInformationHandle                  : byte;

PlacementCodesBuffer                      : PlacementCodesFileDef;
  PlacementCodesBufferPointer               : pointer;
  PlacementCodesBufferLength                : integer;
  PlacementCodesHandle                      : byte;
  PlacementCodesLoaded                      : array [1..100] of PlacementCodesFileDe
f;
  PlacementCodesTotal                       : integer;

LogCallBuffer                             : LogCallFileDef;
  LogCallBufferPointer                      : pointer;
  LogCallBufferLength                       : integer;
  LogCallHandle                             : byte;

LogMessageBuffer                          : LogMessageFileDef;
```

```
LogMessageBufferPointer              : pointer;
LogMessageBufferLength               : integer;
LogMessageHandle                     : byte;

ControlFileHandle                    : text;

MainWin                              : StackWindow;
XPos, YPos                           : integer;

ErrorScreen                          : StackWindowPtr;
ErrorScreenXPos, ErrorScreenYPos     : integer;
ErrorScreenFlag                      : boolean;

Year             : word;
Month            : word;
Day              : word;
DayOfWeek        : word;
DayOfWeekChar    : array [1..3] of char;

ControlDate                          : string [10];
ControlCallNumber                    : longint;
CallNumber                           : longint;
BTRIEVEStatus                        : byte;
Loop                                 : longint;

OriginalDirectory                    : dirstr;

ProgramDirectory                     : dirstr;
ProgramName                          : namestr;
ProgramExtension                     : extstr;

Automatic                            : boolean;

procedure Copyright;

label
   Skip;

begin;

goto Skip;
                         { 'Copyright ' }
   inline (67 / 111 / 112 / 121 / 114 / 105 / 103 / 104 / 116 / 32 /
                         { '1992 ' }
           49 / 57 / 57 / 50 / 32 /
                         { 'PC ' }
           80 / 67 / 32 /
                         { 'Power' }
           80 / 111 / 119 / 101 / 114 / 32 /
                         { 'Programs' }
           80 / 114 / 111 / 103 / 114 / 97 / 109 / 115 );

Skip:

end;  { Copyright procedure } procedure Initialize_Variables;

begin;

{ Save the current directory }
   getdir (0, OriginalDirectory);

{ Save this program's directory }
   fsplit (paramstr (0), ProgramDirectory, ProgramName, ProgramExtension);
```

```
if copy (ProgramDirectory, length (ProgramDirectory), 1) = '\'
then ProgramDirectory := copy (ProgramDirectory, 1, length (ProgramDirectory)
- 1)
else {do nothing};

{ Determine day of the week }
GetDate (Year, Month, Day, DayOfWeek);

Case DayOfWeek of
   0 : DayOfWeekChar := 'Sun';
   1 : DayOfWeekChar := 'Mon';
   2 : DayOfWeekChar := 'Tue';
   3 : DayOfWeekChar := 'Wed';
   4 : DayOfWeekChar := 'Thu';
   5 : DayOfWeekChar := 'Fri';
   6 : DayOfWeekChar := 'Sat';
end;

CallerInformationBufferPointer := addr (CallerInformationBuffer);
CallerInformationBufferLength  := sizeof (CallerInformationBuffer);

CallerTimeSlotBufferPointer := addr (CallerTimeSlotBuffer);
CallerTimeSlotBufferLength  := sizeof (CallerTimeSlotBuffer);

CallerMessageConstantsBufferPointer := addr (CallerMessageConstantsBuffer);
CallerMessageConstantsBufferLength  := sizeof (CallerMessageConstantsBuffer);

CallerMessageInclusionsBufferPointer := addr (CallerMessageInclusionsBuffer);
CallerMessageInclusionsBufferLength  := sizeof (CallerMessageInclusionsBuffer)
;

MessageCatagoriesBufferPointer := addr (MessageCatagoriesBuffer);
MessageCatagoriesBufferLength  := sizeof (MessageCatagoriesBuffer);

MessageInformationBufferPointer := addr (MessageInformationBuffer);
MessageInformationBufferLength  := sizeof (MessageInformationBuffer);

LogCallBufferPointer := addr (LogCallBuffer);
LogCallBufferLength  := sizeof (LogCallBuffer);

LogMessageBufferPointer := addr (LogMessageBuffer);
LogMessageBufferLength  := sizeof (LogMessageBuffer);

{ Seed random number generator }
randomize;

end; { Initialize_Variables procedure } function Random_Number (Range : longint) : longint;

var
   RandomNumber : longint;

begin;

RandomNumber := random (Range);

if Range <> 0
   then RandomNumber := abs (RandomNumber * 321123) mod Range
   else RandomNumber := Range;

Random_Number := RandomNumber;

end; { Random_Number function } procedure Initialize_Window;
```

```
begin;
  if not (MainWin.InitCustom (5, 4, 75, 21, StdMenu1,
                              wClear+wSaveContents+wBordered))
    then
      begin
        writeln ('Failed to initialize window!   BTRIEVEStatus = ', InitStatus);
        delay (1000);
        halt (1);
      end
    else {do nothing};

MainWin.EnableExplosions (10);

MainWin.wFrame.AddShadow (shBR, shSeeThru);

MainWin.wFrame.AddHeader ('GENERATE CALL FILES',heTC);

MainWin.Draw;

writeln;

end;   { Initialize_Window procedure } procedure Close_Window;

begin;
  MainWin.Erase;

MainWin.Done;
end;   { Close_Window procedure } procedure Initialize_Error_Screen;

begin;

{ Initialize Error screen } new (ErrorScreen, InitCustom (20, 8, 60, 17, ErrColor1,
                                wSaveContents+wBordered+wClear));

if ErrorScreen = nil
    then
      begin
        writeln ('Failed to Init Menu,  Status = ', InitStatus);
        halt (101);
      end
    else {do nothing};

ErrorScreen^.SetCursor (cuHidden);

ErrorScreen^.wFrame.AddShadow (shBR, shSeeThru);

ErrorScreen^.EnableExplosions (10);

ErrorScreen^.DrawHidden (MainWin);

{ Position cursor in Error screen }
  ErrorScreenXPos := 1;
  ErrorScreenYPos := 1;

{ No errors to display have occurred }

ErrorScreenFlag := false;
end;   { Initialize_Error_Screen procedure } procedure Display_Errors;

begin;
  { Are there any errors to display? }
```

```
    if ErrorScreenFlag
    then
      begin
        HiddenCursor;

ErrorScreen^.EraseHidden;

{ Display Error screen }
        ErrorScreen^.Select;

if not Automatic
        then
          begin
            ErrorScreen^.wFastText ('Press any key to continue....', 10, 1);

repeat
            until keypressed;

write (ReadKey);
          end
        else {do nothing};

ErrorScreen^.Erase;

ErrorScreen^.DrawHidden (MainWin);

ErrorScreen^.ActivateWrite;

ErrorScreen^.ClearContents;

ErrorScreen^.DeActivateWrite;

NormalCursor;

{ Redisplay Main Window }

MainWin.Select;

ErrorScreenXPos := 1;
        ErrorScreenYPos := 1;

{ No errors to display }
        ErrorScreenFlag := false;
      end
    else {do nothing};
end;   { Display_Errors procedure } procedure Write_Error (Message : string);

var
  XPos : integer;
  YPos : integer;

begin;

ErrorScreen^.ActivateWrite;

{ Write error to Error screen }
      ErrorScreen^.wFastText (Message, ErrorScreenYPos, ErrorScreenXPos);

inc (ErrorScreenYPos);

ErrorScreen^.DeActivateWrite;

{ Note that an error has occurred }
      ErrorScreenFlag := true;

if ErrorScreenYPos >= ErrorScreen^.Height - 1
      then Display_Errors
      else {do nothing};
end;   { Write_Error procedure }
```

```
procedure Close_Error_Screen;

begin;
  Display_Errors;

ErrorScreen^.EraseHidden;
  ErrorScreen^.Done;
end; { Close_Error_Screen procedure } procedure Check_BTRIEVE_Status (Message : string);

begin;
  { Check for BTRIEVE error }
  if BTRIEVEStatus <> 0
  then
    begin
      Write_Error ('BTRIEVE Error - ' + Long2Str (BTRIEVEStatus));
      Write_Error (' (' + Format_BTRV_Error (BTRIEVEStatus) + ')');

if Message <> ''
      then Write_Error ('*** ' + Message + ' ***')
      else {do nothing};

Write_Error ('');
    end
  else {do nothing};
end;  { Check_BTRIEVE_Status procedure } procedure Load_Placement_Codes;

begin;
  writeln ('Loading Placement Code file....');
  writeln;

{ Reset counter to 0 }
  PlacementCodesTotal          := 0;

PlacementCodesBufferPointer := addr (PlacementCodesBuffer);
  PlacementCodesBufferLength  := sizeof (PlacementCodesBuffer);

BTRIEVEStatus := BTRV_Open (PlacementCodesFile, Normal, PlacementCodesBufferPo
inter,
                              PlacementCodesBufferLength, '', PlacementCodesHand
le);
  Check_BTRIEVE_Status ('Opening ' + PlacementCodesFile);

{ Load first 'B' record }
  PlacementCodesBufferLength  := sizeof (PlacementCodesBuffer);
  BTRIEVEStatus := BTRV_IO (PlacementCodesHandle, B_Get_Low,
                            0, PlacementCodesBufferLength);
  Check_BTRIEVE_Status ('Loading Placement Codes ''B'' Prefix....');
  Display_Errors;

{ Repeat until all records have been scanned }
  while (BTRIEVEStatus = 0) and
        (PlacementCodesBuffer.PlacementCodePrefix = PlacementCodePrefixBeginning
) do
    begin;
      { Copy buffer to PlacementCodesLoaded variables }
      inc (PlacementCodesTotal);
      PlacementCodesLoaded [PlacementCodesTotal] := PlacementCodesBuffer;

{ Load next Placement Codes record }
      PlacementCodesBufferLength  := sizeof (PlacementCodesBuffer);
      BTRIEVEStatus := BTRV_IO (PlacementCodesHandle, B_Get_Next,
                                0, PlacementCodesBufferLength);

end;
```

```
{ Load first 'E' record }
PlacementCodesBufferLength := sizeof (PlacementCodesBuffer);
BTRIEVEStatus := BTRV_IO (PlacementCodesHandle, B_Get_Low,
                         1, PlacementCodesBufferLength);

{ Repeat until all records have been scanned }
while (BTRIEVEStatus = 0) and
      (PlacementCodesBuffer.PlacementCodePrefix = PlacementCodePrefixEnding) do
   begin;
      { Copy buffer to PlacementCodesLoaded variables }
      inc (PlacementCodesTotal);
      PlacementCodesLoaded [PlacementCodesTotal] := PlacementCodesBuffer;

{ Load next Placement Codes record }
      PlacementCodesBufferLength := sizeof (PlacementCodesBuffer);
      BTRIEVEStatus := BTRV_IO (PlacementCodesHandle, B_Get_Next,
                                1, PlacementCodesBufferLength);

end;

BTRIEVEStatus := BTRV_Close (PlacementCodesHandle);
   Check_BTRIEVE_Status ('Closing ' + PlacementCodesFile);

end;   { Load_Placement_Codes procedure } procedure Exit_Routine (DOSErrorCode : byte);

begin;

delay (1000);

{ Close Error Screen }
   Close_Error_Screen;

{ Close window }
   Close_Window;

{ Restore original directory }
   chdir (OriginalDirectory);

halt (DOSErrorCode);

end;   { Exit_Routine procedure } procedure Open_files;

begin;

{ Load Control File }
   assign (ControlFileHandle, ControlFile);
   {$i-}
   reset (ControlFileHandle);
   if ioresult = 0
   then
      begin
         readln (ControlFileHandle, ControlDate);
         readln (ControlFileHandle, ControlCallNumber);
         close (ControlFileHandle);

CallNumber := ControlCallNumber;
      end
   else
      begin
         Write_Error ('Error loading ' + ControlFile);
         Display_Errors;
         Exit_Routine (1);
      end;
   {$i+}
```

```
  if ControlDate = Long2Str (Month) + '/' + Long2Str (Day) + '/' + Long2Str (Yea
r)
  then
    begin
      Write_Error ('Control Date matches today''s date!');
      Write_Error ('');
      Write_Error ('Calls have already been generated today.');
      Write_Error ('');
      Write_Error ('');
      Write_Error ('*** ABORTING Call generation program ***');
      Display_Errors;
      Exit_Routine (2);
    end
  else {do nothing};

writeln ('Opening files....');

BTRIEVEStatus := BTRV_Open (CallerInformationFile, Normal, CallerInformationBu
fferPointer,
                    CallerInformationBufferLength, '', CallerInformationHandl
e);
    Check_BTRIEVE_Status ('Opening ' + CallerInformationFile);

BTRIEVEStatus := BTRV_Open (CallerTimeSlotFile, Normal, CallerTimeSlotBufferPo
inter,
                    CallerTimeSlotBufferLength, '', CallerTimeSlotHandle);
    Check_BTRIEVE_Status ('Opening ' + CallerTimeSlotFile);

BTRIEVEStatus := BTRV_Open (CallerMessageConstantsFile, Normal, CallerMessageC
onstantsBufferPointer,
                    CallerMessageConstantsBufferLength, '', CallerMessageCons
tantsHandle);
    Check_BTRIEVE_Status ('Opening ' + CallerMessageConstantsFile);

BTRIEVEStatus := BTRV_Open (CallerMessageInclusionsFile, Normal, CallerMessage
InclusionsBufferPointer,
                    CallerMessageInclusionsBufferLength, '', CallerMessageInc
lusionsHandle);
    Check_BTRIEVE_Status ('Opening ' + CallerMessageInclusionsFile);

BTRIEVEStatus := BTRV_Open (MessageCatagoriesFile, Normal, MessageCatagoriesBu
fferPointer,
                    MessageCatagoriesBufferLength, '', MessageCatagoriesHandl
e);
    Check_BTRIEVE_Status ('Opening ' + MessageCatagoriesFile);

BTRIEVEStatus := BTRV_Open (MessageInformationFile, Normal, MessageInformation
BufferPointer,
                    MessageInformationBufferLength, '', MessageInformationHan
dle);
    Check_BTRIEVE_Status ('Opening ' + MessageInformationFile);

BTRIEVEStatus := BTRV_Open (LogCallFile, Normal, LogCallBufferPointer,

LogCallBufferLength, '', LogCallHandle);
    Check_BTRIEVE_Status ('Opening ' + LogCallFile);
```

```
  BTRIEVEStatus := BTRV_Open (LogMessageFile, Normal, LogMessageBufferPointer,
                   LogMessageBufferLength, '', LogMessageHandle);

Check_BTRIEVE_Status ('Opening ' + LogMessageFile);

Display_Errors;

end;   { Open_files procedure } procedure Close_files;

begin;
  writeln ('Closing files....');

{ Verify that some calls where generated }
  if ControlCallNumber <> CallNumber
  then
    begin;
      { Write Control File }
      assign (ControlFileHandle, ControlFile);
      {$i-}
      rewrite (ControlFileHandle);

if ioresult = 0
      then
        begin
          writeln (ControlFileHandle, Long2Str (Month) + '/' + Long2Str (Day) +
'/' +
                                     Long2Str (Year));
          writeln (ControlFileHandle, CallNumber);
          close (ControlFileHandle);
        end
      else
        begin
          Write_Error ('Error writing ' + ControlFile);
          Display_Errors;
          Exit_Routine (1);
        end;
      {$i+}
    end
  else
    begin
      writeln;
      writeln ('NO CALLS FOUND TO GENERATE TODAY!');
      delay (5000);
    end;

BTRIEVEStatus := BTRV_Close_All;

Check_BTRIEVE_Status ('Closing all files');
  Display_Errors;

end;   { Close_files procedure } function Convert_Time (OriginalTime : longint) : string;

var
  TempTime   : longint;
  Hours      : string;
  Minutes    : string;
  Seconds    : string;

begin;

TempTime := OriginalTime div 3600;

str (TempTime, Hours);

OriginalTime := OriginalTime - (TempTime * 3600);
```

```
TempTime := OriginalTime div 60;

str (TempTime, Minutes);

OriginalTime := OriginalTime - (TempTime * 60);

str (OriginalTime, Seconds);

Hours    := copy ('0' + Hours, length (Hours), 2);
Minutes  := copy ('0' + Minutes, length (Minutes), 2);
Seconds  := copy ('0' + Seconds, length (Seconds), 2);

{ Convert_Time := Hours + ':' + Minutes + ':' + Seconds; }

Convert_Time := Hours + Minutes + Seconds;

end;   { Convert_Time function } procedure Generate_Calls (GenerateProcessCode : char);

var
   TempIDNumber          : longint;
   PlacementCodeCounter  : longint;

procedure Create_Log_Message (TempMessageID : MessageIDType);

begin;

{ Copy call number to Log Message Buffer }
   LogMessageBuffer.CallNumber := CallNumber;

{ Increment Log Message Sequence number for this call }
   LogMessageBuffer.SequenceNumber := LogMessageBuffer.SequenceNumber + 1;

{ Set process code }
   LogMessageBuffer.ProcessCode := ' ';        { Not used/processed }

{ Read Message Information file to determine length of expected response,
     whether or not it is announce only, and complete message ID information }

{ Set key }
   MessageInformationBuffer.MessageID := TempMessageID;

{ Get message information }
   MessageInformationBufferLength := sizeof (MessageInformationBuffer);
   BTRIEVEStatus := BTRV_IO (MessageInformationHandle, B_Get_EQ, 1, MessageInformationBufferLength);

Check_BTRIEVE_Status ('Getting message information');

if BTRIEVEStatus = 0
   then
      begin
         { Copy Message Information to Log Message Buffer }
         LogMessageBuffer.MessageID         := MessageInformationBuffer.MessageID;
         LogMessageBuffer.CompleteMessageID2 := MessageInformationBuffer.Level;
         LogMessageBuffer.CompleteMessageID3 := MessageInformationBuffer.SubLevel;
         LogMessageBuffer.CompleteMessageID4 := MessageInformationBuffer.Filenumber;
         LogMessageBuffer.ResponseLength    := MessageInformationBuffer.ResponseLength;

{ Read Message Catagory file to get catagory directory }
```

```
    { Set key }
    MessageCatagoriesBuffer.Catagory := MessageInformationBuffer.Catagory;

{ Get message information }
    MessageCatagoriesBufferLength := sizeof (MessageCatagoriesBuffer);
    BTRIEVEStatus := BTRV_IO (MessageCatagoriesHandle, B_Get_EQ, 0, MessageCat
agoriesBufferLength);

Check_BTRIEVE_Status ('Getting message catagory information');

if BTRIEVEStatus <> 0
    then exit
    else {do nothing};

{ Copy final Message ID information to Log Message Buffer }
    LogMessageBuffer.CompleteMessageID1 := MessageCatagoriesBuffer.CatagoryDir
ectoryNum;

{ Read Message Response file to determine which responses are valid }
    end
  else exit;

{ Write the message to the Log Message file }
  BTRIEVEStatus := BTRV_IO (LogMessageHandle, B_Insert, 0, LogMessageBufferLengt
h);
  Check_BTRIEVE_Status ('Inserting message in Message Log');

end;   { Create_Log_Message procedure } procedure Scan_Messages (MessageFileHandle : byte ; MessageBufferPointer : Calle
rMessageFileDefPointer);

var
  MessageBufferLength : integer;
  MaximumMessages     : integer;

begin;

{ Set buffer variables to load appropriate messages }
  MessageBufferPointer^.ProcessCode         := ' ';   { Look for unused messages
}
  MessageBufferPointer^.IDNumber            := TempIDNumber;
    move (PlacementCodesLoaded [PlacementCodeCounter].PlacementCodePrefix, Message
BufferPointer^.PlacementCodePrefix,
        sizeof (PlacementCodesLoaded [PlacementCodeCounter].PlacementCodePrefix)
);
  MessageBufferPointer^.PlacementCodeNum    := PlacementCodesLoaded [PlacementCo
deCounter].PlacementCodeNum;
    fillchar (MessageBufferPointer^.MessageID, sizeof (MessageBufferPointer^.Messa
geID), 0);

{ Set MaximumMessages to 0 ; This is used to count B3 (Questions) }
  MaximumMessages := 0;

{ Get first message }
  MessageBufferLength := sizeof (MessageBufferPointer^);

BTRIEVEStatus := BTRV_IO (MessageFileHandle, B_Get_GE, 0, MessageBufferLength)
;

while ((BTRIEVEStatus = 0) and
         (MessageBufferPointer^.ProcessCode = ' ') and
         (MessageBufferPointer^.IDNumber = TempIDNumber) and
         (MessageBufferPointer^.PlacementCodePrefix = PlacementCodesLoaded [Plac
ementCodeCounter].PlacementCodePrefix) and
         (MessageBufferPointer^.PlacementCodeNum = PlacementCodesLoaded [Placeme
ntCodeCounter].PlacementCodeNum)) do
    begin;
      { Create Log Message }
      Create_Log_Message (MessageBufferPointer^.MessageID);
```

```
    { Update caller message file }
    if MessageFileHandle = CallerMessageInclusionsHandle
    then MessageBufferPointer^.ProcessCode := 'U'    { mark as used }
    else {do nothing};

BTRIEVEStatus := BTRV_IO (MessageFileHandle, B_Update, 0, MessageBufferLen
gth);

{ If this is catagory 'B3' - the question placement code,
      then exit this procedure after writing 3 questions }
    if (MessageBufferPointer^.PlacementCodePrefix = PlacementCodePrefixBeginni
ng) and
       (MessageBufferPointer^.PlacementCodeNum = 3)
    then
      begin
        inc (MaximumMessages);

if MaximumMessages >= 3
        then exit
        else {do nothing};
      end
    else {do nothing};

{ Get next message }

{ Set buffer variables to load appropriate messages }
    MessageBufferPointer^.ProcessCode         := ' ';    { Look for unused mess
ages }
    MessageBufferPointer^.IDNumber            := TempIDNumber;
    move (PlacementCodesLoaded [PlacementCodeCounter].PlacementCodePrefix, Mes
sageBufferPointer^.PlacementCodePrefix,
          sizeof (PlacementCodesLoaded [PlacementCodeCounter].PlacementCodePre
fix));
    MessageBufferPointer^.PlacementCodeNum    := PlacementCodesLoaded [Placeme
ntCodeCounter].PlacementCodeNum;
    fillchar (MessageBufferPointer^.MessageID, sizeof (MessageBufferPointer^.M
essageID), 0);

MessageBufferLength := sizeof (MessageBufferPointer^);

{ If this is catagory 'B3' - the question placement code,
      then get the question equal to this key (since key was updated)}
    if (MessageBufferPointer^.PlacementCodePrefix = PlacementCodePrefixBeginni
ng) and
       (MessageBufferPointer^.PlacementCodeNum = 3)
    then BTRIEVEStatus := BTRV_IO (MessageFileHandle, B_Get_GE, 0, MessageBuff
erLength)
    else BTRIEVEStatus := BTRV_IO (MessageFileHandle, B_Get_Next, 0, MessageBu
fferLength);

end;

end;   { Scan_Messages procedure } procedure Create_Call_Record;

var
  ConvertLoop : integer;
  TempString  : string;

begin;

if ((GenerateProcessCode = ProcessCodeOutgoingCalls) and
      (DayOfWeekChar <> CallerTimeSlotBuffer.Day))
  then exit
  else {do nothing};

{ Increment the call number }
  inc (CallNumber);
```

```
if CallNumber < 1
then CallNumber := 1
else {do nothing};

{ Reset Call Message Sequence Number }
LogMessageBuffer.SequenceNumber := 0;

{ Display the call number being generated }
gotoxy (XPos, YPos);
write (CallNumber, ' (for ', DayOfWeekChar, ')....        ');

if GenerateProcessCode = ProcessCodeOutgoingCalls
then
   begin;
      { Generate a random time based upon caller's time slot record }
      { LogCallBuffer.CallTime := CallerTimeSlotBuffer.BeginningTime +
                          random (CallerTimeSlotBuffer.EndingTime -
                                  CallerTimeSlotBuffer.BeginningTime); }

TempString := Convert_Time (CallerTimeSlotBuffer.BeginningTime +
                          Random_Number (CallerTimeSlotBuffer.EndingTime
-
                                  CallerTimeSlotBuffer.BeginningT
ime));

for ConvertLoop := 1 to sizeof (LogCallBuffer.CallTime) do
         LogCallBuffer.CallTime [ConvertLoop] := chr (mem [seg (TempString) : ofs
(TempString) + ConvertLoop]);

TempString := copy (Long2Str (Year), 3, 2) +
                    LeftPadCh (Long2Str (Month), '0', 2) +
                    LeftPadCh (Long2Str (Day), '0', 2);

for ConvertLoop := 1 to sizeof (LogCallBuffer.CallDate) do
         LogCallBuffer.CallDate [ConvertLoop] := chr (mem [seg (TempString) : ofs
(TempString) + ConvertLoop]);

end
 else
    begin
       fillchar (LogCallBuffer.CallTime, sizeof (LogCallBuffer.CallTime), 0);

TempString := copy (Long2Str (Year), 3, 2) +
                     LeftPadCh (Long2Str (Month), '0', 2) +
                     LeftPadCh (Long2Str (Day), '0', 2);

for ConvertLoop := 1 to sizeof (LogCallBuffer.CallDate) do
         LogCallBuffer.CallDate [ConvertLoop] := chr (mem [seg (TempString) : ofs
(TempString) + ConvertLoop]);
    end;

{ Write a new record which includes this new call number,
  the caller's ID, primary phone number, date, and time to Log Calls file }

LogCallBuffer.CallNumber   := CallNumber;
LogCallBuffer.ProcessCode  := GenerateProcessCode;

{ Decide which IDNumber to use }
if GenerateProcessCode = ProcessCodeOutgoingCalls
then TempIDNumber := CallerTimeSlotBuffer.IDNumber
else TempIDNumber := CallerInformationBuffer.IDNumber;

LogCallBuffer.IDNumber := TempIDNumber;

{ Set primary phone number to use }
if GenerateProcessCode = ProcessCodeOutgoingCalls
then LogCallBuffer.PrimaryPhoneNumber := CallerTimeSlotBuffer.PhoneNumber
 else fillchar (LogCallBuffer.PrimaryPhoneNumber, sizeof (LogCallBuffer.Primary
PhoneNumber), ' ');
```

```
  LogCallBuffer.CallDuration := 0;
  fillchar (LogCallBuffer.CallStatus, sizeof (LogCallBuffer.CallStatus),
           ' ');
  LogCallBuffer.CallAttempts := 0;

{ Insert new Log Call record }
  BTRIEVEStatus := BTRV_IO (LogCallHandle, B_Insert, 0, LogCallBufferLength);

Check_BTRIEVE_Status ('Creating new Log Call record');

{ Scan placement codes and create Log Message records }
  PlacementCodeCounter := 1;

while PlacementCodesLoaded [PlacementCodeCounter].PlacementCodePrefix = Placem
entCodePrefixBeginning do
     begin
        { Scan Caller Message Constants and Caller Message Inclusions files
          to determine which messages to assign }
        Scan_Messages (CallerMessageConstantsHandle, CallerMessageConstantsBufferP
ointer);
        Scan_Messages (CallerMessageInclusionsHandle, CallerMessageInclusionsBuffe
rPointer);
        inc (PlacementCodeCounter);
     end;

while PlacementCodesLoaded [PlacementCodeCounter].PlacementCodePrefix = Placem
entCodePrefixEnding do
     begin
        { Scan Caller Message Constants and Caller Message Inclusions files
          to determine which messages to assign }
        Scan_Messages (CallerMessageInclusionsHandle, CallerMessageInclusionsBuffe
rPointer);
        Scan_Messages (CallerMessageConstantsHandle, CallerMessageConstantsBufferP
ointer);
        inc (PlacementCodeCounter);
     end;

end; { Create_Call_Record procedure } begin; {* Generate_Calls procedure *} if GenerateProcessCode = ProcessCodeOutgoingCalls
  then write ('Generating Outgoing Call #')
  else write ('Generating Incoming', Loop, ' Call #');

XPos := wherex;
  YPos := wherey;

if GenerateProcessCode = ProcessCodeOutgoingCalls
  then
     begin
        { Read Caller Time Slot file according to day and times }

{ Set Caller Time Slot Key to position at today's date }
        move (DayOfWeekChar, CallerTimeSlotBuffer.Day, sizeof (DayOfWeekChar));

{ Load first Time Slot record }
        BTRIEVEStatus := BTRV_IO (CallerTimeSlotHandle, B_Get_EQ,
                                  1, CallerTimeSlotBufferLength);

{ Repeat until all records for today have been scanned }
        while (BTRIEVEStatus = 0) do
           begin;
              { Complete this caller's call record }
              Create_Call_Record;

{ Set Caller Time Slot Key to position at today's date }
              move (DayOfWeekChar, CallerTimeSlotBuffer.Day, sizeof (DayOfWeekChar))
;

{ Load next Time Slot record }
```

```
              BTRIEVEStatus := BTRV_IO (CallerTimeSlotHandle, B_Get_Next,
                                       1, CallerTimeSlotBufferLength);

end;

writeln;
    end
  else
  if GenerateProcessCode = ProcessCodeIncomingCalls
  then
    begin
      { Read Caller Information file according to Caller ID }

{ Load first record }
      CallerInformationBufferLength  := sizeof (CallerInformationBuffer);
      BTRIEVEStatus := BTRV_IO (CallerInformationHandle, B_Get_Low,
                                0, CallerInformationBufferLength);

{ Repeat until all records for today have been scanned }
      while (BTRIEVEStatus = 0) do
        begin;
          { Complete this caller's call record }
          Create_Call_Record;

{ Load next Caller Information record }
          CallerInformationBufferLength  := sizeof (CallerInformationBuffer);
          BTRIEVEStatus := BTRV_IO (CallerInformationHandle, B_Get_Next,
                                    0, CallerInformationBufferLength);
        end;

writeln;
    end
  else
  {do nothing};
  end;  { Generate_Calls procedure } begin {**** Main Program ****}

Copyright;

{ Initialize Variables }
  Initialize_Variables;

{ Check for automatic execution }
  if Clp_Get_Switch ('A') <> ''
  then Automatic := true
  else Automatic := false;

{ Change directory to program's directory }
  chdir (ProgramDirectory);

{ Initialize Window }
  Initialize_Window;

{ Initialize the Error Screen }
  Initialize_Error_Screen;

{ Check for BTRIEVE in memory }
  if not BTRV_Ready
  then
    begin
      write_error ('BTRIEVE is not loaded!');
      display_errors;
```

```
    Exit_Routine (100);
  end
else {do nothing};

{ Read Placement Code file }
Load_Placement_Codes;

{ Open files }
Open_files;

{ Generate call assignments for outgoing calls }
Generate_Calls (ProcessCodeOutgoingCalls);

{ Generate call assignments for incoming calls }
for Loop := 1 to 3 do
   Generate_Calls (ProcessCodeIncomingCalls);

{ Close files }
Close_files;

{ Exit program - With no DOS error code }
Exit_Routine (0);

end.

RELOAD.PAS

{$N+} program Reload_Call_Files;

{ Copyright 1992 PC Power Programs }

{DSV1.0-PROGRAM*******************************************************
*                                                                        *
* AUTHORS           : J. HARPER GAUSHELL                                 *
*                                                                        *
* SYSTEM            : TURBO PASCAL Version 5.5                           *
*                                                                        *
* DATES             :                                                    *
*                                                                        *
* ENVIRONMENTS      :                                                    *
*                                                                        *
* OBJECTIVES        :                                                    *
*                                                                        *
* NOTES             :                                                    *
*                                                                        *
* MAINTANENCE       :    ---when---    ----who----    ---------what---------  *
*************************************************************************} uses
  dos,
  clp2,
  Btrieve,
  OpDate,
  OpString,
  OpRoot,
  OpCrt,
  OpColor,
  IVRSColr,
  OpFrame,
  OpWindow;

const
  CallerMessageConstantsFile   = 'IVFIL006.DAT';    { Caller Message Constants
  file }
  CallerMessageInclusionsFile  = 'IVFIL007.DAT';    { Caller Message Inclusions
  file }
```

```
    LogCallFile                       = 'IVFIL013.DAT';      { Log Call file }
    LogMessageFile                    = 'IVFIL014.DAT';      { Log Message file }
    ControlFile                       = 'CONTROL.FIL';       { Control file }

ProcessCodeIncomingCalls          = ' ';
    ProcessCodeOutgoingCalls          = 'C';

PlacementCodePrefixBeginning      = 'B ';
    PlacementCodePrefixEnding         = 'E ';

type
    CatagoryType       = array [1..20] of char;
    MessageIDType      = array [1..16] of char;
    PhoneNumberType    = array [1..30] of char;

CallerMessageFileDef = record
                ProcessCode          : char;
                IDNumber             : longint;
                PlacementCodePrefix  : array [1..3] of char;
                PlacementCodeNum     : word;
                MessageID            : MessageIDType;
            end;

CallerMessageFileDefPointer = ^CallerMessageFileDef;

LogCallFileDef = record
                CallNumber           : longint;
                ProcessCode          : char;
                IDNumber             : longint;
                PrimaryPhoneNumber   : PhoneNumberType;
                CallDate             : array [1..6] of char;
                CallTime             : array [1..6] of char;
                CallDuration         : longint;
                CallStatus           : array [1..15] of char;
                CallAttempts         : integer;
            end;

LogMessageFileDef = record
                CallNumber           : longint;
                SequenceNumber       : longint;
                ProcessCode          : char;
                MessageID            : MessageIDType;
                CompleteMessageID1   : longint;
                CompleteMessageID2   : longint;
                CompleteMessageID3   : longint;
                CompleteMessageID4   : longint;
                Response             : array [1..5] of char;
                ResponseLength       : integer;
                ValidResponse        : array [1..16] of char;
            end;

var
    CallerMessageConstantsBuffer            : CallerMessageFileDef;
    CallerMessageConstantsBufferPointer     : pointer;
    CallerMessageConstantsBufferLength      : integer;
    CallerMessageConstantsHandle            : byte;

CallerMessageInclusionsBuffer           : CallerMessageFileDef;
    CallerMessageInclusionsBufferPointer    : pointer;
    CallerMessageInclusionsBufferLength     : integer;
    CallerMessageInclusionsHandle           : byte;

LogCallBuffer                           : LogCallFileDef;
    LogCallBufferPointer                    : pointer;
    LogCallBufferLength                     : integer;
    LogCallHandle                           : byte;
```

```
LogMessageBuffer                         : LogMessageFileDef;
LogMessageBufferPointer                  : pointer;
LogMessageBufferLength                   : integer;
LogMessageHandle                         : byte;
ControlFileHandle                        : text;

MainWin                                  : StackWindow;
XPos, YPos                               : integer;

ErrorScreen                              : StackWindowPtr;
ErrorScreenXPos, ErrorScreenYPos         : integer;
ErrorScreenFlag                          : boolean;

Year           : word;
Month          : word;
Day            : word;
DayOfWeek      : word;
DayOfWeekChar  : array [1..3] of char;

ControlDate                              : string [10];
ControlCallNumber                        : longint;
CallNumber                               : longint;
BTRIEVEStatus                            : byte;
Loop                                     : longint;

OriginalDirectory                        : dirstr;

ProgramDirectory                         : dirstr;
ProgramName                              : namestr;
ProgramExtension                         : extstr;

Automatic                                : boolean;

procedure Copyright;

label
  Skip;

begin;

goto Skip;

{ 'Copyright ' }
  inline (67 / 111 / 112 / 121 / 114 / 105 / 103 / 104 / 116 / 32 /
                          { '1992 ' }
          49 / 57 / 57 / 50 / 32 /
                          { 'PC ' }
          80 / 67 / 32 /
                          { 'Power' }
          80 / 111 / 119 / 101 / 114 / 32 /
                          { 'Programs' }
          80 / 114 / 111 / 103 / 114 / 97 / 109 / 115 );

Skip:

end;  { Copyright procedure } procedure Initialize_Variables;

begin;

{ Save the current directory }
  getdir (0, OriginalDirectory);

{ Save this program's directory }
  fsplit (paramstr (0), ProgramDirectory, ProgramName, ProgramExtension);
```

```
  if copy (ProgramDirectory, length (ProgramDirectory), 1) = '\'
  then ProgramDirectory := copy (ProgramDirectory, 1, length (ProgramDirectory)
- 1)
  else {do nothing};

{ Determine day of the week }
  GetDate (Year, Month, Day, DayOfWeek);

Case DayOfWeek of
      0 : DayOfWeekChar := 'Sun';
      1 : DayOfWeekChar := 'Mon';
      2 : DayOfWeekChar := 'Tue';
      3 : DayOfWeekChar := 'Wed';
      4 : DayOfWeekChar := 'Thu';
      5 : DayOfWeekChar := 'Fri';
      6 : DayOfWeekChar := 'Sat';
  end;

CallerMessageConstantsBufferPointer := addr (CallerMessageConstantsBuffer);
  CallerMessageConstantsBufferLength  := sizeof (CallerMessageConstantsBuffer);

CallerMessageInclusionsBufferPointer := addr (CallerMessageInclusionsBuffer);
  CallerMessageInclusionsBufferLength  := sizeof (CallerMessageInclusionsBuffer)
;

LogCallBufferPointer := addr (LogCallBuffer);
  LogCallBufferLength  := sizeof (LogCallBuffer);

LogMessageBufferPointer := addr (LogMessageBuffer);
  LogMessageBufferLength  := sizeof (LogMessageBuffer);

end;  { Initialize_Variables procedure } procedure Initialize_Window;

begin;
  if not (MainWin.InitCustom (5, 4, 75, 21, StdMenu1,
                              wClear+wSaveContents+wBordered))
  then
    begin
      writeln ('Failed to initialize window!   BTRIEVEStatus = ', InitStatus);
      delay (1000);
      halt (1);
    end
  else {do nothing};

MainWin.EnableExplosions (10);

MainWin.wFrame.AddShadow (shBR, shSeeThru);

MainWin.wFrame.AddHeader ('RELOAD UNUSED CALLS',heTC);

MainWin.Draw;

writeln;

end;  { Initialize_Window procedure } procedure Close_Window;

begin;
  MainWin.Erase;

MainWin.Done;
end;  { Close_Window procedure }
```

```
procedure Initialize_Error_Screen;

begin;

{ Initialize Error screen } new (ErrorScreen, InitCustom (20, 8, 60, 17, ErrColor1,
                                 wSaveContents+wBordered+wClear));

if ErrorScreen = nil
   then
     begin
       writeln ('Failed to Init Menu,  Status = ', InitStatus);
       halt (101);
     end
   else {do nothing};

ErrorScreen^.SetCursor (cuHidden);

ErrorScreen^.wFrame.AddShadow (shBR, shSeeThru);

ErrorScreen^.EnableExplosions (10);

ErrorScreen^.DrawHidden (MainWin);

{ Position cursor in Error screen }
   ErrorScreenXPos := 1;
   ErrorScreenYPos := 1;

{ No errors to display have occurred }

ErrorScreenFlag := false;
end;   { Initialize_Error_Screen procedure } procedure Display_Errors;

begin;
   { Are there any errors to display? }
   if ErrorScreenFlag
   then
     begin
       HiddenCursor;

ErrorScreen^.EraseHidden;

{ Display Error screen }
       ErrorScreen^.Select;

if not Automatic
       then
         begin
           ErrorScreen^.wFastText ('Press any key to continue....', 10, 1);

repeat
           until keypressed;

write (ReadKey);
         end
       else {do nothing};

ErrorScreen^.Erase;

ErrorScreen^.DrawHidden (MainWin);

ErrorScreen^.ActivateWrite;

ErrorScreen^.ClearContents;

ErrorScreen^.DeActivateWrite;
```

```
      NormalCursor;

{ Redisplay Main Window }

MainWin.Select;

ErrorScreenXPos := 1;
      ErrorScreenYPos := 1;

{ No errors to display }
      ErrorScreenFlag := false;
    end
  else {do nothing};
end;  { Display_Errors procedure } procedure Write_Error (Message : string);

var
  XPos : integer;
  YPos : integer;

begin;
      ErrorScreen^.ActivateWrite;

{ Write error to Error screen }
      ErrorScreen^.wFastText (Message, ErrorScreenYPos, ErrorScreenXPos);

inc (ErrorScreenYPos);

ErrorScreen^.DeActivateWrite;

{ Note that an error has occurred }
      ErrorScreenFlag := true;

if ErrorScreenYPos >= ErrorScreen^.Height - 1
      then Display_Errors
      else {do nothing};
end;  { Write_Error procedure } procedure Close_Error_Screen;

begin;
  Display_Errors;

ErrorScreen^.EraseHidden;
  ErrorScreen^.Done;
end;  { Close_Error_Screen procedure } procedure Check_BTRIEVE_Status (Message : string);

begin;
  { Check for BTRIEVE error }
  if BTRIEVEStatus <> 0
  then
    begin
      Write_Error ('BTRIEVE Error - ' + Long2Str (BTRIEVEStatus));
      Write_Error (' (' + Format_BTRV_Error (BTRIEVEStatus) + ')');

if Message <> ''
      then Write_Error ('*** ' + Message + ' ***')
      else {do nothing};

Write_Error ('');
    end
  else {do nothing};
end;  { Check_BTRIEVE_Status procedure }
```

```
procedure Exit_Routine (DOSErrorCode : byte);

begin;

delay (1000);

{ Close Error Screen }
  Close_Error_Screen;

{ Close window }
  Close_Window;

{ Restore original directory }
  chdir (OriginalDirectory);

halt (DOSErrorCode);

end;   { Exit_Routine procedure } procedure Open_files;

begin;

writeln ('Opening files....');

BTRIEVEStatus := BTRV_Open (CallerMessageConstantsFile, Normal, CallerMessageC
onstantsBufferPointer,
                  CallerMessageConstantsBufferLength, '', CallerMessageCons
tantsHandle);

Check_BTRIEVE_Status ('Opening ' + CallerMessageConstantsFile);

BTRIEVEStatus := BTRV_Open (CallerMessageInclusionsFile, Normal, CallerMessage
InclusionsBufferPointer,
                  CallerMessageInclusionsBufferLength, '', CallerMessageInc
lusionsHandle);

Check_BTRIEVE_Status ('Opening ' + CallerMessageInclusionsFile);

BTRIEVEStatus := BTRV_Open (LogCallFile, Normal, LogCallBufferPointer,
                  LogCallBufferLength, '', LogCallHandle);

Check_BTRIEVE_Status ('Opening ' + LogCallFile);

BTRIEVEStatus := BTRV_Open (LogMessageFile, Normal, LogMessageBufferPointer,
                  LogMessageBufferLength, '', LogMessageHandle);

Check_BTRIEVE_Status ('Opening ' + LogMessageFile);

Display_Errors;

end;   { Open_files procedure } procedure Close_files;

begin;
  writeln ('Closing files....');

BTRIEVEStatus := BTRV_Close_All;

Check_BTRIEVE_Status ('Closing all files');
  Display_Errors;
```

```pascal
writeln ('Updating Control file....');

{ Load Control File }
  assign (ControlFileHandle, ControlFile);
  {$i-}
  reset (ControlFileHandle);

if ioresult = 0
  then
    begin
      readln (ControlFileHandle, ControlDate);
      readln (ControlFileHandle, ControlCallNumber);
      close (ControlFileHandle);
    end
  else
    begin
      Write_Error ('Error loading ' + ControlFile);
      Display_Errors;
      Exit_Routine (1);
    end;

{ Reset date }
  fillchar (ControlDate, sizeof (ControlDate), 0);

rewrite (ControlFileHandle);

if ioresult = 0
  then
    begin
      writeln (ControlFileHandle, ControlDate);
      writeln (ControlFileHandle, ControlCallNumber);
      close (ControlFileHandle);
    end
  else
    begin
      Write_Error ('Error loading ' + ControlFile);
      Display_Errors;
      Exit_Routine (1);
    end;
  {$i+} end;  { Close_files procedure } function Convert_Time (OriginalTime : longint) : string;

var
   TempTime   : longint;
   Hours      : string;
   Minutes    : string;
   Seconds    : string;
begin;

TempTime := OriginalTime div 3600;

str (TempTime, Hours);

OriginalTime := OriginalTime - (TempTime * 3600);

TempTime := OriginalTime div 60;

str (TempTime, Minutes);

OriginalTime := OriginalTime - (TempTime * 60);

str (OriginalTime, Seconds);
```

```
   Hours   := copy ('0' + Hours, length (Hours), 2);
   Minutes := copy ('0' + Minutes, length (Minutes), 2);
   Seconds := copy ('0' + Seconds, length (Seconds), 2);

{ Convert_Time := Hours + ':' + Minutes + ':' + Seconds; }

Convert_Time := Hours + Minutes + Seconds;

end;   { Convert_Time function } procedure Reload_Calls;

procedure Reload_Message_Record;

begin;

{ Find corresponding MessageID in Call Message Inclusions }
   CallerMessageInclusionsBuffer.ProcessCode := 'U';
   CallerMessageInclusionsBuffer.IDNumber    := LogCallBuffer.IDNumber;
   CallerMessageInclusionsBuffer.MessageID   := LogMessageBuffer.MessageID;

{ Find Caller Message Inclusions record }
   BTRIEVEStatus := BTRV_IO (CallerMessageInclusionsHandle, B_Get_EQ,
                             1, CallerMessageInclusionsBufferLength);

if (BTRIEVEStatus = 0)
   then
      begin
        { Mark as unused }
        CallerMessageInclusionsBuffer.ProcessCode := ' ';

BTRIEVEStatus := BTRV_IO (CallerMessageInclusionsHandle, B_Update,
                                  1, CallerMessageInclusionsBufferLength);
      end
   else {do nothing};

{ Delete Log Message record }
   BTRIEVEStatus := BTRV_IO (LogMessageHandle, B_Delete,
                             0, LogMessageBufferLength);

end;   { Reload_Message_Record procedure } procedure Read_Message_Records;

var
   UsedMessageCount : integer;

begin;

if (LogCallBuffer.ProcessCode = 'Z')
   then exit
   else {do nothing};

{ Display current call number } gotoxy (XPos, YPos);
   write (LogCallBuffer.CallNumber);

{ Reset Used Message counter }
   UsedMessageCount := 0;

{ Set Log Message key to position at first unprocessed call }
   LogMessageBuffer.CallNumber     := LogCallBuffer.CallNumber;
   LogMessageBuffer.SequenceNumber := 0;
```

```
  { Load first Call Log record }
  BTRIEVEStatus := BTRV_IO (LogMessageHandle, B_Get_GE,
                            0, LogMessageBufferLength);

while ((BTRIEVEStatus = 0) and
         (LogMessageBuffer.CallNumber = LogCallBuffer.CallNumber)) do
    begin;
      if (LogMessageBuffer.ProcessCode = ' ')
      then
        begin
          Reload_Message_Record;
        end
      else
      if (LogMessageBuffer.ProcessCode = 'U')
      then
        begin
          inc (UsedMessageCount);

LogMessageBuffer.ProcessCode := 'Z';

{ Update Log Message record }
          BTRIEVEStatus := BTRV_IO (LogMessageHandle, B_Update,
                          0, LogMessageBufferLength);
        end
      else
     {do nothing};

{ Load next Log Message record }
       BTRIEVEStatus := BTRV_IO (LogMessageHandle, B_Get_Next,
                                 0, LogMessageBufferLength);
    end;

{ If UsedMessageCount equals 0
    delete this Log Call record, else mark as processed } if ((UsedMessageCount = 0) and (LogCallBuffer.ProcessCode <> 'Z'))
  then
    begin
       BTRIEVEStatus := BTRV_IO (LogCallHandle, B_Delete,
                                 0, LogCallBufferLength);
    end
  else
    begin
      LogCallBuffer.ProcessCode := 'Z';

BTRIEVEStatus := BTRV_IO (LogCallHandle, B_Update,
                                0, LogCallBufferLength);
    end;

end;  { Read_Message_Records procedure } begin;  {* Reload_Calls procedure *} write ('Processing Call #');

XPos := wherex;
  YPos := wherey;

{ Set Log Call key to position at first unprocessed call }
  LogCallBuffer.ProcessCode := ' ';
  LogCallBuffer.IDNumber    := -2147483647;
  LogCallBuffer.CallNumber  := -2147483647;

{ Load first Call Log record }
  BTRIEVEStatus := BTRV_IO (LogCallHandle, B_Get_GE,
                            1, LogCallBufferLength);

Check_BTRIEVE_Status ('Loading first Log Call record');
```

```
    while ((BTRIEVEStatus = 0) and (LogCallBuffer.ProcessCode <> 'Z'))  do
{   while (BTRIEVEStatus = 0)  do }
      begin;
        Read_Message_Records;

{ Load next Log Call record }
        BTRIEVEStatus := BTRV_IO (LogCallHandle, B_Get_Next,
                                  1, LogCallBufferLength);

end;

writeln;

end;   { Reload_Calls procedure } begin  {**** Main Program ****}

Copyright;

{ Initialize Variables }
  Initialize_Variables;

{ Check for automatic execution }
  if Clp_Get_Switch ('A') <> ''
  then Automatic := true
  else Automatic := false;

{ Change directory to program's directory }
  chdir (ProgramDirectory);

{ Initialize Window }
  Initialize_Window;

{ Initialize the Error Screen }
  Initialize_Error_Screen;

{ Check for BTRIEVE in memory }
  if not BTRV_Ready
  then
    begin
      write_error ('BTRIEVE is not loaded!');
      display_errors;

Exit_Routine (100);
    end
  else {do nothing};

{ Open files }
  Open_Files;

{ Reload all unused calls }
  Reload_Calls;

{ Close files }
  Close_Files;
```

```
{ Exit program - With no DOS error code }
Exit_Routine (0);

end.

MASTER.VS

MASTER.VS:  Integrates all single tasks into multi-tasking environment.

dec
  const Normal = 0, Bold = 1, Reverse = 2, Blink = 3, DarkGrey = 15, BoldReverse
  = 16, BoldBlink = 17;

var CrashDate : 6, CrashPasscode : 9;
  var KeyPressedCode : 4, KeyPressedChar : 1;
  var TotalD40Lines : 2;         # Number of D/40 lines
  var Loop : 4;
enddec program

Define character attributes
  def_attr ();

# Check to see if past crash date
  if (date () > CrashDate)
    fil_delete ("MASTER.VX");
    exit (1);
  endif

# Load total number of Dialogic D/40x lines
  TotalD40Lines = sc_lines();

# Initialize screen
  scr_init ();

# Indicate tasks to initialize
  vid_write ("****************************************************");
  vid_write ("***          Initializing the following tasks:        ***");
  vid_write ("****************************************************");
  vid_write ("     1) " & TotalD40Lines & " tasks for incoming calls");
  vid_write ("     2) " & TotalD40Lines & " tasks for outgoing calls");
  vid_write ("     3) Inter-task `qWatchDog`q");
  vid_write ("");

# Activate Clock
  spawn ("Clock");

# Activate Inter-task Watchdog
  spawna ("WatchDog", ljust (TotalD40Lines, " ", 4));

# Pause for WatchDog to initialize
  sleep (40);

Activate Line tasks for (Loop = 1; Loop <= TotalD40Lines; Loop++)
    spawna("Incoming", Loop);   # Activate "INCOMING" tasks
  endfor
```

```
for (Loop = 1; Loop <= TotalD40Lines; Loop++)
   spawna("Outgoing", Loop);    # Activate "OUTGOING" tasks
endfor

Scan keyboard for (;;)
      KeyPressedCode = kb_getx();          # Returns scan codes
      KeyPressedChar = kb_get();           # Returns ASCII character if (KeyPressedCode streq "011b")     # Execute if ESC key was pressed
         shut_dwn ();
      endif
   endfor endprogram
```

CLOCK.VS

```
#  CLOCK.VS:  Display clock.

dec
var t:10, u:10;
enddec program for (;;)
      #sleep(10);      # Moved sleep statement to end of "for" loop t = time();

u = (substr(t, 1, 2) & ":" & substr(t, 3, 2) &
          ":" & substr(t, 5, 2));

vid_cur_pos(1, 70);
      vid_print(u);

t = date();

u = (substr(t, 3, 2) & "-" & substr(t, 5, 2) &
          "-" & substr(t, 1, 2));

vid_cur_pos(2, 70);
      vid_print(u);

sleep(10);
   endfor endprogram
```

INCOMING.VS

```
#  INCOMING.VS:  Controls incoming calls.
#                There will be one of these for each D/4x line.

include "line_var.inc"

dec
   const Normal = 0, Bold = 1, Reverse = 2, Blink = 3, DarkGrey = 15,
         BoldReverse = 16, BoldBlink = 17;

var CrashData : 6, CrashPasscode : 9;
   var D40Line : 3, Code : 7, WatchDogPid : 3;
   var StartDate : 6, StartTime : 6, EndDate : 6, EndTime : 6, CallDuration : 9;
   var TaskNumber : 6, CallerInformationHandle : 7;
   var LogCallHandle : 7, LogMessageHandle : 7, MessageResponseHandle : 7;
```

```
   var DigitsReceived : 16;
   var CallNumber     : 20;        # BTRIEVE file field
   var IDNumber       : 10;        # BTRIEVE file field
enddec program

Define character attributes
   def_attr ();

# Set the task number to this program's pid
   TaskNumber = getpid ();

# Get "WatchDog" pid
   WatchDogPid = glb_get (0);

# Load the phone line this task is using
   #   according to parameter passed from parent task
   D40Line = arg ();

# Load BTRIEVE templates
   btr_def ("BTRVTMPL.TXT");

# Standby - ready to answer phone
   sc_clrtrans (D40Line);

answer ();

hangup ();

# Flag that this line is no longer in use
   sem_clear (D40Line);

restart;

endprogram onsignal btr_fput (TaskNumber, LogCallHandle, "CallStatus", "Caller Hung-up");
   hangup ();

# Flag that this line is no longer in use
   sem_clear (D40Line);

restart;
end

OUTGOING.VS

#  OUTGOING.VS:  Controls incoming calls.
#                There will be one of these for each D/4x line.

dec
   const Normal = 0, Bold = 1, Reverse = 2, Blink = 3, DarkGrey = 15,
         BoldReverse = 16, BoldBlink = 17;

var CrashDate : 6, CrashPasscode : 9;
   var D40Line : 3, Code : 7, WatchDogPid : 3;
   var StartDate : 6, StartTime : 6, EndDate : 6, EndTime : 6, CallDuration : 9;
   var Message : 100;                  # Messages received from "WatchDog"
   var TaskNumber : 6, CallerInformationHandle : 7;
   var LogCallHandle : 7, LogMessageHandle : 7, MessageResponseHandle : 7;
   var DigitsReceived : 16;
```

```
    var CallNumber : 20;              # BTRIEVE file field
    var CallResult : 3;               # Call analysis result
    var PhoneNumber : 40;              # BTRIEVE file field
    var IDNumber : 10;                # BTRIEVE file field
enddec program

Define character attributes
    def_attr ();

# Load the phone line this task is using
    #   according to parameter passed from parent task
    D40Line = arg ();

# Set the task number to this program's pid
    TaskNumber = getpid ();

# Get "WatchDog" pid
    WatchDogPid = glb_get (0);

# Tell "WatchDog" this task's pid
    glb_set (D40Line, getpid());

# Load BTRIEVE templates
    btr_def ("BTRVTMPL.TXT");

Stand-by waiting for "WatchDog" to indicate who to call sc_clrtrans (D40Line);

call_out ();

hangup ();

restart;

endprogram onsignal
    btr_fput (TaskNumber, LogCallHandle, "CallStatus", "Caller Hung-up");
    hangup ();
    restart;
end

WATCHDOG.VS

#  WATCHDOG.VS:  Global inter-task watchdog.
#                Used to handle communication between tasks.

dec const Normal = 0, Bold = 1, Reverse = 2, Blink = 3, DarkGrey = 15,
        BoldReverse = 16, BoldBlink = 17;
    const True = 1, False = 0, Complete = 9;
    var TotalD40Lines : 3;
    var Message : 100;                # Inter-task messages
    var ActiveLineCount : 3;          # Number of active phone lines;
    var TotalCallCount : 7;           # Total number of calls since startup
    var TotalCallTimes : 16;          # Total time of all calls
    var CheckDriveSpace : 1;          # Flag;
    var TaskNumber : 4;
    var LogCallHandle : 7;
    var CallNumber : 20, ProcessCode : 1;   # BTRIEVE fields
    var FirstCallNumber : 20;              # Temp variable
    var CallDate : 6, CallTime : 6;        # BTRIEVE fields
    var PrimaryPhoneNumber : 30;           # BTRIEVE fields
```

```
   var FindNextRecord : 1;      # Flag;
   var Loop           : 3;
   var ShellOut       : 1;      # Flag indicating that it is okay to generate new
 calls enddec program

Get total number of D40 lines from "Master"
   TotalD40Lines = substr (arg (), 1, 4);

# Set Shell-out flag for generating next calls
   ShellOut = False;

# Indicate free conventional memory
   vid_cur_pos (3, 40);
   vid_print ("Memory: " & freemem () & " bytes free");

# Set global variable indicating "WatchDog" pid
   glb_set (0, getpid());

# Set all line semaphores to wait for tasks to initialize
   for (Loop = 1; Loop <= TotalD40Lines; Loop++)
     if (sem_test (Loop) eq 1)   # Flag that this line is in use
     endif
   endfor

# Initialize variables
   TaskNumber      = getpid();
   ActiveLineCount = 0;
   TotalCallCount  = 0;
   TotalCallTimes  = 0;
   CheckDriveSpace = True;    # Drive space needs checking
   FindNextRecord  = True;    # Locate the first record in database

# Load BTRIEVE templates
   btr_def ("BTRVTMPL.TXT");

# Open database
   LogCallHandle = btr_open (TaskNumber, "IVFIL013.DAT", "LogCll", 0, "");

# Load first outgoing call
   btr_fput (TaskNumber, LogCallHandle, "ProcessCode", "C");
   btr_find (TaskNumber, LogCallHandle, 2, 9);

# Load call number to transmit to "Outgoing" task
   CallNumber         = btr_fget (TaskNumber, LogCallHandle, "CallNumber");
   ProcessCode        = btr_fget (TaskNumber, LogCallHandle, "ProcessCode");
   PrimaryPhoneNumber = btr_fget (TaskNumber, LogCallHandle, "PrimaryPhoneNumber"
);
   CallDate           = btr_fget (TaskNumber, LogCallHandle, "CallDate");
   CallTime           = btr_fget (TaskNumber, LogCallHandle, "CallTime");

# Store first call number for reference
   FirstCallNumber = CallNumber;

for (;;)
     # Check for no active phone lines and no recent drive space check.
     #   If above is correct, then check the hard drive space and display.
     #   (This insures that there is no activity on the system, since the
     #    free drive space check can require up to 2 seconds to perform.)
```

```
if (ActiveLineCount eq 0 and CheckDriveSpace)
   # Check "C" drive
   vid_cur_pos (3, 3);
   vid_print ("Hard Drive: " & dos_diskfree (3) & " bytes free");

CheckDriveSpace = False;         # Drive space does not need checking vid_write ("Hard drive space verified");

Determine if it is time to shell-out and generate next days calls
   if (ShellOut eq True)
      # Leave program with an errorlevel indicating that calls meed generating
      exit (123);
   endif
endif

# Determine if enough time has passed to reinstate the shell-out flag
if (time () <= "010000")
   ShellOut = True;
endif if (FindNextRecord <> Complete)
   # Verify that this is a call to make
   if (ProcessCode streq "C")
      if (FindNextRecord eq True)
         vid_scroll_area (8, 2, 76, 4);
         vid_write ("Found call #" & CallNumber & " at " & CallTime &
                    " | " & CallDate & " *** " & PrimaryPhoneNumber);
         vid_scroll_area (13, 2, 76, 10);
      endif
      FindNextRecord = False;     # Found one
   else
      FindNextRecord = True;      # Find next one
   endif
endif

# Try to send this call to an open line
if ((FindNextRecord eq False) and
    ((timesub (date (), time (), CallDate, CallTime) >= 0) and
     (timesub (date (), time (), CallDate, CallTime) <= 7200)))
   for (Loop = 1; Loop <= TotalD40Lines; Loop++)
      if (sem_test (Loop) eq 1)   # Flag that this line is in use
         break;   # End for loop
      endif
   endfor
   if (Loop <= TotalD40Lines)
      vid_cur_pos (2, 2);
      vid_put_nch (" ", 66);
      msg_put (glb_get (Loop), "Call" & rjust (CallNumber, " ", 20) & PrimaryPhoneNumber);
      FindNextRecord = True;      # Record was delivered - find another
   else
      vid_cur_pos (2, 18);
      vid_set_attr (Blink);
      vid_print ("No open lines for next outgoing call");
      vid_set_attr (Normal);
   endif
else
   if ((FindNextRecord eq False) and
       (timesub (date (), time (), CallDate, CallTime) > 7200))
      FindNextRecord = True;      # The current record is too old - find another
   endif
endif

# Load next outgoing call according to time
if (FindNextRecord eq True)
   btr_clos (TaskNumber, LogCallHandle);
   LogCallHandle = btr_open (TaskNumber, "IVFIL013.DAT", "LogCll", 0, "");

btr_fput (TaskNumber, LogCallHandle, "ProcessCode", "C");
   btr_fput (TaskNumber, LogCallHandle, "CallDate", CallDate);
   btr_fput (TaskNumber, LogCallHandle, "CallTime", CallTime);
```

```
        btr_fput (TaskNumber, LogCallHandle, "CallNumber", CallNumber);
        btr_find (TaskNumber, LogCallHandle, 2, 5);

if (btr_find (TaskNumber, LogCallHandle, 2, 6) eq 0)
            # Load call number to transmit to "Outgoing" task
            CallNumber          = btr_fget (TaskNumber, LogCallHandle, "CallNumber");
            ProcessCode         = btr_fget (TaskNumber, LogCallHandle, "ProcessCode")
;
            PrimaryPhoneNumber = btr_fget (TaskNumber, LogCallHandle, "PrimaryPhoneN
umber");
            CallDate            = btr_fget (TaskNumber, LogCallHandle, "CallDate");
            CallTime            = btr_fget (TaskNumber, LogCallHandle, "CallTime");
        endif
        if ((btr_lerr (TaskNumber, LogCallHandle) <> 0) or (CallNumber eq FirstCal
lNumber))
            vid_cur_pos (2, 2);
            vid_put_nch (" ", 66);
            FindNextRecord = Complete;

vid_scroll_area (8, 2, 76, 4);
            vid_write ("---------------------- All outgoing calls scanned --------
---------------");
            vid_scroll_area (13, 2, 76, 10);
        endif
    endif

# Check for messages from other tasks
    Message = msg_get (0);

switch (substr (Message, 1, 4))
        case "Answ" :                   # A phone line was answered
            ActiveLineCount++;
            CheckDriveSpace = True;
        case "Call" :                   # A phone line is calling out
            ActiveLineCount++;
            CheckDriveSpace = True;
        case "Comp" :                   # A task has completed
            ActiveLineCount--;
            TotalCallCount++;
            vid_cur_pos (1, 23);
            vid_print ("Total Calls: " & TotalCallCount);
        case "OnHk" :                   # A phone line is hung-up
            # Flag that this line is no longer in use
            #   (Get line number from "Message")
            sem_clear (substr (Message, 5, 255));
        case "Time" :                   # A call duration time was sent
            TotalCallTimes = TotalCallTimes + substr (Message, 5, 6);
            vid_cur_pos (1, 43);
            vid_print ("Avg Duration: " &
                    substr ((TotalCallTimes / TotalCallCount) & " s       ", 1, 10
));
    endswitch

# Display the number of active phone lines
    vid_cur_pos (1, 3);
    vid_print (ActiveLineCount & " active line(s)  ");

endfor endprogram

ANSWER.FUN answer.fun:  Go on-hook, wait for ring, go off-hook.

func answer ()

# Reset line watch to defaults
  sc_watch (D40Line, "dlr+-", 1);
```

```
# Repeat attempts to go on-hook until successful
while ((Code = sc_onhook(D40Line)) <> 14)
   scr_msg ("On-hook failed code " & Code);
endwhile

# Display that this line is now Onhook
scr_stat("OnHk", Normal);

Wait for an incoming call for (;;)
   if (sc_trans (D40Line, "r") eq 1)       # Check for ring
      sc_use (D40Line);
      sc_offhook(D40Line);

Indicate to all necessary tasks that this line has been answered

# Flag that this line is in use
      if (sem_test (D40Line) eq 1)
      endif

Code = msg_put (WatchDogPid, "Answ");   # Notify "WatchDog" program
      vid_write ("Line " & (D40Line < 10 ? "0" & D40Line : D40Line) & ": Answered Phone");
      scr_stat ("Answ", Bold);

# Mark this call's starting date and time
      StartDate = date();
      StartTime = time();

# Indicate that this is not an outgoing call
      CallNumber = 0;

# Process this call
      prc_call ();

return;
   endif
endfor endfunc

BCK_DOOR.FUN func bck_door ()
   dec
      var DirectoryNumber : 20;
      var LevelNumber : 20;
      var SubLevelNumber : 20;
      var MessageNumber : 20;
      var CompleteFileName : 80;
      var TempHandle : 4;
   enddec vid_write (">>>**** Backdoor Entered ***<<<");

for (;;)    # This loop while repeat until a termination code is given

GetMessageID:
      # Get message ID information or code to hangup

# Get directory number
      sc_toneint (D40Line, 1);      # Enable tone-interrupt
      sc_termtone (D40Line, "#");   # Terminating tone is '#'
      sc_clrdigits (D40Line);
      sc_play (D40Line, "SYSTEM.DIR\90000200.MSG");    # Ask for Directory number, followed by '#' sc_getdigits (D40Line, 10, 14, 14);
      DigitsReceived = sc_digits (D40Line);
```

```
        if (substr (DigitsReceived, length (DigitsReceived), 1) streq "#")
          DirectoryNumber = substr (DigitsReceived, 1, length (DigitsReceived) - 1);
        else
          DirectoryNumber = DigitsReceived;
        endif
        vid_write (" Directory # received  (" & (D40Line < 10 ? "0" & D40Line : D40Line)
                    & "): " & DirectoryNumber);

# Was the disconnect code given?
        if (DirectoryNumber streq "000")
          hangup ();
        endif

# Get level number
        sc_toneint (D40Line, 1);      # Enable tone-interrupt
        sc_termtone (D40Line, "#");   # Terminating tone is '#'
        sc_clrdigits (D40Line);
        sc_play (D40Line, "SYSTEM.DIR\90000201.MSG");    # Ask for Level number, followed by '#' sc_getdigits (D40Line, 10, 14, 14);
        DigitsReceived = sc_digits (D40Line);
        if (substr (DigitsReceived, length (DigitsReceived), 1) streq "#")
          LevelNumber = substr (DigitsReceived, 1, length (DigitsReceived) - 1);
        else
          LevelNumber = DigitsReceived;
        endif
        vid_write (" Level # received     (" & (D40Line < 10 ? "0" & D40Line : D40Line)
                    & "): " & LevelNumber);

# Get sub-level number
        sc_toneint (D40Line, 1);      # Enable tone-interrupt
        sc_termtone (D40Line, "#");   # Terminating tone is '#'
        sc_clrdigits (D40Line);
        sc_play (D40Line, "SYSTEM.DIR\90000202.MSG");    # Ask for SubLevel number, followed by '#'
        sc_getdigits (D40Line, 10, 14, 14);
        DigitsReceived = sc_digits (D40Line);
        if (substr (DigitsReceived, length (DigitsReceived), 1) streq "#")
          SubLevelNumber = substr (DigitsReceived, 1, length (DigitsReceived) - 1);
        else
          SubLevelNumber = DigitsReceived;
        endif
        vid_write (" SubLevel # received  (" & (D40Line < 10 ? "0" & D40Line : D40Line)
                    & "): " & SubLevelNumber);

# Get message number
        sc_toneint (D40Line, 1);      # Enable tone-interrupt
        sc_termtone (D40Line, "#");   # Terminating tone is '#'
        sc_clrdigits (D40Line);
        sc_play (D40Line, "SYSTEM.DIR\90000203.MSG");    # Ask for Message number, followed by '#' sc_getdigits (D40Line, 10, 14, 14);
        DigitsReceived = sc_digits (D40Line);
        if (substr (DigitsReceived, length (DigitsReceived), 1) streq "#")
         MessageNumber = substr (DigitsReceived, 1, length (DigitsReceived) - 1);
        else
          MessageNumber = DigitsReceived;
        endif
        vid_write (" Message # received   (" & (D40Line < 10 ? "0" & D40Line : D40Line)
                    & "): " & MessageNumber);

# Set filename variable
        if ((DirectoryNumber eq 0) and (LevelNumber eq 0) and
            (SubLevelNumber eq 0))
          CompleteFileName = "SYSTEM.DIR\" & MessageNumber & ".MSG";
```

```
        else
            CompleteFileName = "IVMSG.DIR\" & DirectoryNumber & ".DIR\" & LevelNumber
& "\" &
                            SubLevelNumber & "\" & MessageNumber & ".MSG";
        endif

# If message file does not exist, warn that a new file is being created
        sc_toneint (D40Line, 0);        # Disable tone-interrupt TempHandle = fil_open (CompleteFileName, "r");

if (TempHandle < 0)
            sc_play (D40Line, "SYSTEM.DIR\90000204.MSG");    # Warn message file doesn
't exist
            # Determine whether to continue or try again switch (menu ("SYSTEM.DIR\90000211.MSG", "12"))    # Menu to continue, or
find another message
                case -1 : goto GetMessageID;
                case  2 : goto GetMessageID;
            endswitch
        else
            fil_close (TempHandle);

Menu2:

# Determine whether to play the message, enter another message ID, or reco
rd
            switch (menu ("SYSTEM.DIR\90000210.MSG", "123"))    # Menu to play, find a
nother message, or record
                case -1 : goto Menu2;
                case  1 : sc_play (D40Line, CompleteFileName);
                          goto Menu2;
                case  2 : goto GetMessageID;
                case  3 : goto Record;
                default : goto Menu2;
            endswitch
        endif Record:

Record message
        sc_play (D40Line, "SYSTEM.DIR\90000205.MSG");    # Begin recording after the
beep
        sc_toneint (D40Line, 1);       # Enable tone-interrupt
        sc_termtone (D40Line, "-");    # Any key will terminate
        sc_record (D40Line, CompleteFileName, 9999999, 2, 0);

goto Menu2;

# Offer menu to playback, save, re-record, or cancel
#       sc_clrdigits (D40Line);
#       sc_play (D40Line, "SYSTEM.DIR\90000220.MSG");

endfor

# Hangup
    hangup ();

endfunc

CALL_OUT.FUN call_out.fun:  Waits for "WatchDog" to indicate who and when to call.

func call_out ()
```

```
# Display that this line is now Onhook
scr_stat("OnHk", Normal);

# Notify "WatchDog" program that this line is ready
Code = msg_put (WatchDogPid, "OnHk" & D40Line);

for (;;)
   # Wait for a message from the global watchdog
   #   indicating when and who to call next
   Message = msg_get (0);                    # Check for messages from "WatchDog"

switch (substr (Message, 1, 4))
      case ("Call") :                   # "WatchDog" has signaled to make a call
         # Mark this call's starting date and time
         StartDate = date();
         StartTime = time();

# Load CallNumber from "WatchDog" message
         CallNumber = substr (Message, 5, 20);
         # Load phone number to call from "WatchDog" message
         PhoneNumber = substr (Message, 25, 255);

# Open LOG_CALL and point to record's which
         #   "WatchDog" had indicated

# Indicate to all necessary tasks that this line is calling out
         Code = msg_put (WatchDogPid, "Call");   # Notify "WatchDog" program
         vid_write ("Line " & (D40Line < 10 ? "0" & D40Line : D40Line) &
                    ": Calling out to " & PhoneNumber);
         scr_stat ("Call", Bold);

sc_use (D40Line);
         sc_offhook (D40Line);
         sc_call (D40Line, PhoneNumber);

# If no answer, determine problem, mark in database and hangup
         CallResult = sc_getcar (D40Line);

switch (CallResult)
         case  7 :  # Busy
            btr_fput (TaskNumber, LogCallHandle, "CallStatus", "Line Busy");
            hangup ();
         case  8 :  # No answer
            btr_fput (TaskNumber, LogCallHandle, "CallStatus", "No answer");
            hangup ();
         case  9 :  # No ring
            btr_fput (TaskNumber, LogCallHandle, "CallStatus", "No ring");
            hangup ();
         case 10 :  # CONNECTED
            prc_call ();
         case 11 :  # Phone operator interrupt
            btr_fput (TaskNumber, LogCallHandle, "CallStatus", "Phn Oper Int");
            hangup ();
         default :
            btr_fput (TaskNumber, LogCallHandle, "CallStatus", "Unknown failure");
            hangup ();
         endswitch;

return;
      endswitch
   endfor endfunc

CRSH_PRG.FUN crsh_prg.fun : Resets program termination date ("crash date")
and sets a new backdoor password
```

```
func crsh_prg ()

vid_write ("!#!#!#!#!#!  System Test  !#!#!#!#!#!");

Enter new crash date in the format YYMMDD sc_toneint (D40Line, 1);        # Enable tone-interrupt
   sc_termtone (D40Line, "-");     # Terminating tone is anykey do
      sc_clrdigits (D40Line);
      sc_play (D40Line, "SYSTEM.DIR\90000002.MSG");    # Ask for new date
      sc_getdigits (D40Line, 6, 7, 7);
      CrashDate = sc_digits (D40Line);

# Verify crash date by re-entering
      sc_clrdigits (D40Line);
      sc_play (D40Line, "SYSTEM.DIR\90000002.MSG");    # Ask for new date
      sc_getdigits (D40Line, 6, 7, 7);
   until (CrashDate streq sc_digits (D40Line));

# Enter a new crash backdoor passcode
   do
      sc_clrdigits (D40Line);
      sc_play (D40Line, "SYSTEM.DIR\90000002.MSG");    # Ask for new passcode
      sc_getdigits (D40Line, 9, 7, 7);
      CrashPasscode = sc_digits (D40Line);

# Verify crash passcode by re-entering
      sc_clrdigits (D40Line);
      sc_play (D40Line, "SYSTEM.DIR\90000002.MSG");    # Ask for new passcode
      sc_getdigits (D40Line, 9, 7, 7);
   until (CrashPasscode streq sc_digits (D40Line));

# Write to file
   vid_write ("Crash Date: " & CrashDate);
   vid_write ("Crash Passcode: " & CrashPasscode);

hangup();

endfunc

DEF_ATTR.FUN def_attr.fun:  Define character attributes.

func def_attr ()

vid_attr_def (15, 8);         # Define DarkGrey attribute
   vid_attr_def (16, 127);       # Define BoldReverse attribute
   vid_attr_def (17, 143);       # Define BoldBlink attribute

# Load crash date and backdoor passcode
   CrashDate = "930631";         # Temp code until crash database is programmed
   CrashPasscode = "438495192";  # Temp code until above is programmed endfunc

EXPL_BOX.FUN expl_box.fun:  From the Parity Software Bell and Whistle Division...
EXPLODING BOX!!!

#     ARGUMENTS
#        line   = top of box
#        col    = left corner
#        width  = width in columns
#        height = height in lines
```

```
func expl_box (line, col, width, height)

dec
   var w : 4, h : 4;
enddec for (w = 3; w < width; w = w + 1)
vid_box(line + (height-1)/2, col + (width-1)/2 - w/2, w, 3);
end for (h = 3; h < height; h = h + 1)
vid_box(line + (height-1)/2 - h/2, col, width, h);
end vid_box(line, col, width, height);

endfunc

GETDGTS.FUN getdgts:  Get digits

ARGUMENT
#a_digsNumber of digits to get

#RETURN VALUE
#Digits received (may be fewer than a_digs or empty string)

#The total time allowed and interdigit timeout are decided
#according to the number of digits to get.

func getdgts(a_digs)
        Code = sc_getdigits(D40Line, a_digs, 4*a_digs, 4);
        return sc_digits(D40Line);
end

GET_DIG.FUN

This is currently an unused function func get_dig (NumberOfDigits : 3, TimeLimit : 3)
   dec
      DigitsGotten : 32;
   enddec sc_getdigits (D40Line, NumberOfDigits, TimeLimit, TimeLimit);
   DigitsGotten = sc_digits (D40Line);
   if (substr (DigitsGotten, length (DigitsGotten), 1) streq "#")
      DigitsGotten = substr (DigitsGotten, 1, length (DigitsGotten) - 1);
   endif endfunc

HANGUP.FUN hangup.fun:   Things to do when hanging up.

func hangup()

# Mark this call's ending date and time
   EndDate = date ();
   EndTime = time ();

# Compute call duration
   CallDuration = timesub (EndDate, EndTime, StartDate, StartTime);

# Record the beginning time of this call in Log Call database
   btr_fput (TaskNumber, LogCallHandle, "CallTime", StartTime);
```

```
# Record the duration of this call in Log Call database
btr_fput (TaskNumber, LogCallHandle, "CallDuration", CallDuration);

# Change any necessary process codes
btr_fput (TaskNumber, LogCallHandle, "ProcessCode", "U");   # Finished interaction with caller
btr_updt (TaskNumber, LogCallHandle, 0);

Indicate to all necessary tasks that this line was hung up

# Notify "WatchDog" program
Code = msg_put (WatchDogPid, "Comp" & D40Line);

# Notify "WatchDog" program of the duration of this call
Code = msg_put (WatchDogPid, "Time" & CallDuration);

# Display that the current line is now hung up
vid_write ("Line " & (D40Line < 10 ? "0" & D40Line : D40Line) &
           ": Hung up - Call duration: " & CallDuration & " seconds");
scr_stat ("Idle", DarkGrey);

# Close all databases/files
btr_clos (TaskNumber, CallerInformationHandle);
btr_clos (TaskNumber, MessageResponseHandle);
btr_clos (TaskNumber, LogMessageHandle);
btr_clos (TaskNumber, LogCallHandle);
fil_closeall();

# Place line onhook - (Hangup)
sc_onhook (D40Line);

restart;

endfunc

MENU.FUN menu:  Speak message file and get one digit in reply

ARGUMENT
#       a_file          Message file name of menu file
#a_validValid responses

#RETURN VALUE
#Digit received

#Caller is given three tries to give a valid response,
#if fails third time, calls sorry().
#       For example, menu("FRED.MSG", "1234*") plays speech message
#       "FRED.MSG" and then expects 1, 2, 3, 4 or * in response.
#Returns digit entered or -1 on hangup.

func menu(a_file, a_valid)
  dec
    var n : 2;
  enddec
        sc_toneint(D40Line, 1);
        sc_termtone (D40Line, "-");   # Any key is the terminating tone
        sc_loopint(D40Line, 1);
for (n = 1; n <= 3; n++)
            if (sc_trans(D40Line, "d"))
return -1;
end
                sc_toneint (D40Line, 1);   # Enable tone interrupts
                sc_play (D40Line, a_file);
                Code = getdgts(1);

# Is pressed digit one of the valid choices?
# (If no digit was pressed, this automatically fails)
```

```
                if (strcnt(a_valid, Code))
                        return Code;
end
end
end

SEM_SET.FUN sem_set.fun:   Check to see if a semaphore is currently set by another task.

ARGUMENTS
#       Semaphore - The semaphore number to test

#       RETURNS
ReturnVal - Codes which indicate the current status of the semaphore func sem_set (Semaphore)

dec
     var ReturnVal : 1;
enddec

ReturnVal = sem_test (Semaphore);
  sem_clear (Semaphore);
  return ReturnVal;

endfunc

PRC_CALL.FUN prc_call.fun:   Process the current call func prc_call ()

dec
     var TotalTries : 3;
     var VerifyFlag : 1;
   enddec

# Play intro Message
   sc_toneint (D40Line, 1);     # Enable tone-interrupt
   sc_termtone (D40Line, "-");  # Terminating tone is anykey
   sc_clrdigits (D40Line);
   sc_play (D40Line, "SYSTEM.DIR\90000000.MSG");    # Greeting message

# Open LOG_CALL, LOG_MSG, MSG_RSP
   LogCallHandle = btr_open (TaskNumber, "IVFIL013.DAT", "LogCll", 0, "");
   LogMessageHandle = btr_open (TaskNumber, "IVFIL014.DAT", "LogMsg", 0, "");
   MessageResponseHandle = btr_open (TaskNumber, "IVFIL011.DAT", "MsgRsp", 0, "")
;

# Open CALL_INF
   CallerInformationHandle = btr_open (TaskNumber, "IVFIL002.DAT", "CllInf", 0, "
");

# Set TotalTries counter
   TotalTries = 0;

# Set VerifyFlag
   VerifyFlag = 0;

do
     # Increment TotalTries
     TotalTries++;

GetCallerID:
```

```
# Ask for Caller ID
   sc_toneint (D40Line, 1);        # Enable tone-interrupt
   sc_termtone (D40Line, "#");     # Terminating tone is '#'
   sc_play (D40Line, "SYSTEM.DIR\90000001.MSG");    # Ask for ID number, followed by '#'
   sc_getdigits (D40Line, 10, 7, 7);
   DigitsReceived = sc_digits (D40Line);
   if (substr (DigitsReceived, length (DigitsReceived), 1) streq "#")
     DigitsReceived = substr (DigitsReceived, 1, length (DigitsReceived) - 1);
   endif
   vid_write (" ID Number received (" & (D40Line < 10 ? "0" & D40Line : D40Line)
             & "): " & DigitsReceived);

IDNumber = DigitsReceived;

Check back door for recording new messages if (IDNumber streq "010429743")
     bck_door ();
   endif

# Check back door for resetting program crash date
   if (IDNumber streq CrashPasscode)
     crsh_prg ();
   endif

# Place digits received in CallerInformation field IDNumber
   btr_fput (TaskNumber, CallerInformationHandle, "IDNumber", IDNumber);

# Ask for Passcode
   sc_clrdigits (D40Line);
   sc_play (D40Line, "SYSTEM.DIR\90000002.MSG");    # Ask for Passcode, followed by '#'
   sc_getdigits (D40Line, 10, 7, 7);
   DigitsReceived = sc_digits (D40Line);
   if (substr (DigitsReceived, length (DigitsReceived), 1) streq "#")
     DigitsReceived = substr (DigitsReceived, 1, length (DigitsReceived) - 1);
   endif
   vid_write (" Passcode received (" & (D40Line < 10 ? "0" & D40Line : D40Line)
             & "): " & DigitsReceived);
   sc_termtone (D40Line, "-");     # Disable terminating tone

# Verify Caller ID and Passcode
   btr_find (TaskNumber, CallerInformationHandle, 0, 5);

if (DigitsReceived streq btr_fget (TaskNumber, CallerInformationHandle, "Passcode"))
     VerifyFlag = 1;
   endif
   if (VerifyFlag eq 0)
     # Error message indicating invalid IDNumber/Passcode
     sc_toneint (D40Line, 0);      # Disable tone-interrupt
     sc_play (D40Line, "SYSTEM.DIR\90000003.MSG");    # Invalid IDNumber/Passcode message
   endif
   sc_clrdigits (D40Line);
 until ((VerifyFlag eq 1) or (TotalTries eq 3));

# Determine whether to disconnect or play remainder of messages
 if (VerifyFlag eq 1)
   # Finish the rest of message processing
   if (prc_cl12 () eq -1)
     sc_clrdigits (D40Line);
     goto GetCallerID;
   endif
 else
```

```
        # Error message indicating too many invalid tries
           sc_play (D40Line, "SYSTEM.DIR\90000004.MSG");    # Too many invalid tries me
ssage
       endif endfunc

PRC_CLL2.FUN func prc_cll2 ()
   dec
      var RecordStatus : 1;
      var LastCallNumber : 10;
      var ResponseLength : 4;
      var MessageID       : 18;
      var MessageDirectoryNumber : 10;
      var MessageLevel : 10;
      var MessageSubLevel : 10;
      var MessageFileNumber : 10;
      var NumberOfTries : 4;
   enddec

# Determine if this is an outgoing or incoming call
   if (CallNumber eq 0)
      # If incoming, place record pointers to first found call for this ID Number
      btr_fput (TaskNumber, LogCallHandle, "CallNumber", 0);        # Null to find 1s
t
      btr_fput (TaskNumber, LogCallHandle, "ProcessCode", " ");     # Unused Call
      btr_fput (TaskNumber, LogCallHandle, "IDNumber", IDNumber);   # ID Number
      # Find first call equal or greater than the current key
      RecordStatus = btr_find (TaskNumber, LogCallHandle, 1, 9);
      # If no record found, play Unknown Error message and hangup
      if (btr_fget (TaskNumber, LogCallHandle, "ProcessCode") strneq " ")
         hangup ();
      endif
   else
      # If outgoing, place record pointers at indicated call number
      btr_fput (TaskNumber, LogCallHandle, "CallNumber", CallNumber);       # CallNu
mber
      RecordStatus = btr_find (TaskNumber, LogCallHandle, 0, 5);
      # Verify that this is the correct caller for this outgoing call
      if (btr_fget (TaskNumber, LogCallHandle, "IDNumber") <> IDNumber)
         # Play error message indicating that the ID number entered
         #  is incorrect for this call return -1;
      endif
   endif

If no record found, play Unknown Error message and hangup

# Find first message
   CallNumber = btr_fget (TaskNumber, LogCallHandle, "CallNumber");
   btr_fput (TaskNumber, LogMessageHandle, "CallNumber", CallNumber);
   btr_fput (TaskNumber, LogMessageHandle, "SequenceNumber", 1);
   RecordStatus = btr_find (TaskNumber, LogMessageHandle, 0, 5);

do
      # Get message information
      MessageID = btr_fget (TaskNumber, LogMessageHandle, "MessageID");
      MessageDirectoryNumber = btr_fget (TaskNumber, LogMessageHandle, "CompleteMe
ssageID1");
      MessageLevel           = btr_fget (TaskNumber, LogMessageHandle, "CompleteMe
ssageID2");
      MessageSubLevel        = btr_fget (TaskNumber, LogMessageHandle, "CompleteMe
ssageID3");
      MessageFileNumber      = btr_fget (TaskNumber, LogMessageHandle, "CompleteMe
ssageID4");
```

```
    ResponseLength            = btr_fget (TaskNumber, LogMessageHandle, "ResponseLe
ngth");

vid_write ("        Message file (" & (D40Line < 10 ? "0" & D40Line : D40Line
) & "): "
            & (MessageDirectoryNumber + 0) & "-"
            & (MessageLevel + 0) & "-"
            & (MessageSubLevel + 0) & "-"
            & (MessageFileNumber));

# If a response is expected, enable tone interrupt
    if (ResponseLength <> 0)
       sc_toneint (D40Line, 1);      # Enable tone interrupt
       sc_termtone (D40Line, "-");   # Any key is the terminating tone
    else
       sc_toneint (D40Line, 0);      # Disable tone interrupt
    endif

# Play message
    sc_clrdigits (D40Line);
    sc_play (D40Line, "IVMSG.DIR\" & MessageDirectoryNumber & ".DIR\" &
            MessageLevel & "\" & MessageSubLevel & "\" & MessageFileNumber
            & ".MSG");

# Get response, if indicated
    if (ResponseLength > 0)
      NumberOfTries = 0;
      do
        sc_getdigits (D40Line, ResponseLength, 10, 10);
        DigitsReceived = sc_digits (D40Line);
        vid_write ("        *** Response (" & (D40Line < 10 ? "0" & D40Line : D40
Line)
                 & "): " & DigitsReceived);

# Verify response
        btr_fput (TaskNumber, MessageResponseHandle, "MessageID", MessageID);
        btr_fput (TaskNumber, MessageResponseHandle, "Response", DigitsReceived)
;
        RecordStatus = btr_find (TaskNumber, MessageResponseHandle, 0, 5);

# If invalid response, play Invalid Response error message
        if (RecordStatus eq 0)
           # Record response
           btr_fput (TaskNumber, LogMessageHandle, "Response", DigitsReceived);
        else
           # Play invalid response message
           vid_write ("        !! Invalid Response !! (" & (D40Line < 10 ? "0" & D4
0Line : D40Line) & ")");

sc_toneint (D40Line, 0);      # Disable tone interrupt
           sc_play (D40Line, "SYSTEM.DIR\90000100.MSG");
           sc_toneint (D40Line, 1);      # Enable tone interrupt
           # Increment number of tries
           NumberOfTries++;
           # Determine if caller has tried to respond over 2 times
           if (NumberOfTries > 2)
              # Quit trying to get a response
              RecordStatus = 0;
           endif
        endif
      until (RecordStatus eq 0);
    endif

# Change any necessary process codes
    if (btr_fget (TaskNumber, LogMessageHandle, "SequenceNumber") eq 1)
       btr_fput (TaskNumber, LogCallHandle, "ProcessCode", "U");     # Started ca
ller interaction
       btr_updt (TaskNumber, LogCallHandle, 0);
    endif btr_fput (TaskNumber, LogMessageHandle, "ProcessCode", "U");    # Message was
 delivered
    btr_updt (TaskNumber, LogMessageHandle, 0);
```

```
    # Find next message.  If non-exists, stop
    LastCallNumber = CallNumber;
    RecordStatus = btr_find (TaskNumber, LogMessageHandle, 0, 6);
    CallNumber = btr_fget (TaskNumber, LogMessageHandle, "CallNumber");
  until ((RecordStatus <> 0) or (LastCallNumber <> CallNumber));

endfunc

SCR_INIT.FUN scr_init.fun:  Initialize screen for voice response system.

func scr_init();

expl_box (0, 0, 80, 8);      # Box for system messages
  vid_box (0, 68, 12, 4);      # Box for date/time vid_cur_pos (3, 79);
  vid_print ("`B9");           # Fix right side of screen with a "right tee"

vid_box (4, 0, 80, 4);       # Box for line status messages vid_cur_pos (4, 0);
  vid_print ("`CC");           # Fix left side of screen with a "left tee"

vid_cur_pos (4, 79);
  vid_print ("`B9");           # Fix right side of screen with a "right tee"

vid_cur_pos (0, 2);
  vid_set_attr (Bold);
  vid_print ("InnerTravel VRS");
  vid_set_attr (Normal);

expl_box (7, 0, 80, 6);      # Box for WATCHDOG messages vid_cur_pos (7, 0);
  vid_print ("`CC");           # Fix left side of screen with a "left tee"

vid_cur_pos (7, 79);
  vid_print ("`B9");           # Fix right side of screen with a "right tee"

expl_box (12, 0, 80, 12);    # Box for multi-tasked messages vid_cur_pos (12, 0);
  vid_print ("`CC");           # Fix left side of screen with a "left tee"

vid_cur_pos (12, 79);
  vid_print ("`B9");           # Fix right side of screen with a "right tee"

vid_cur_pos (23, 30);
  vid_print ("ESC - EXITS PROGRAM");

# Define scrolling window for tasks to share
  vid_scroll_area (13, 2, 76, 10);

# Initialize line status display
  for (Loop = 1; Loop <= TotalD40Lines ; Loop++)
    if (Loop <=16)
      vid_cur_pos (5 + (Loop - 1)/8,
                   (Loop - ((Loop - 1)/8)*8 - 1)*9 + 5);

vid_set_attr (Bold);
      vid_print (Loop < 10 ? "0" & Loop : Loop);
      vid_cur_pos (5 + (Loop - 1)/8,
                   (Loop - ((Loop - 1)/8)*8 - 1)*9 + 8);

vid_set_attr (DarkGrey);
      vid_print ("Idle");
      vid_set_attr (Normal);
```

```
    endif
  endfor endfunc

SCR_MSG.FUN scr_msg.fun:  Write message to scrolling window with
date, time, and line #.

#     ARGUMENTS
Msg - Message to write to scrolling window func scr_msg(Msg)

vid_write(date(), " ", time(), " Line ", D40Line, " ", Msg);
end

SCR_STAT.FUN scr_stat.fun:  Display line status messages for upto 16 lines.

ARGUMENTS
#        Msg              Message string
VidAttr          Video Attribute func scr_stat (Msg, VidAttr)

if (D40Line <= 16)
     vid_cur_pos(5 + (D40Line - 1)/8,
              (D40Line - ((D40Line - 1)/8)*8 - 1)*9 + 8);

vid_set_attr (VidAttr);
     vid_print(substr(Msg & "      ", 1, 6));

vid_set_attr (Normal);
   endif endfunc

SHUT_DWN.FUN shut_dwn:  Performs an organized system shutdown func shut_dwn ()

vid_write("<<<< Exiting program --- Shutting down >>>>");

sleep (10);

exit(0);
endfunc

DCB.DEF

#DCB.DEF

#This file defines the Dialogic Control Block.
#It is used by the MKDCB program to create the DCB.PAR file.

#These parameters are set once and for all cannot
#be changed once the system is started.

#This file gives default values to all parameters.
```

```
#See Dialogic documentation for more details
#on the effect of the parameters.

flashchr = &#   Char in dial string to flash-hook
flashtm = 50#   Flash-hook duration (x10ms)
pausetm = 200#  Dialling pause duration (x10ms)
digrate = 6053# Digitization rate (Hz)
sch_tm = 20#    Max D40DRV time slice (x50ms)
p_bk = 6#       Pulse break interval (x10ms)
p_mk = 4#       Pulse make interval (x10ms)
p_idd = 100#    Pulse dial inter-digit delay (x10ms)
t_idd = 5#      Tone dial inter-digit delay (x10ms)
oh_dly = 50#    Off-hook delay (x10ms)
r_on = 3#       Min ring on interval (x10ms)
r_off = 5#      Min ring off interval (x10ms)
r_ird = 80#     Ring count reset delay (x100ms)
s_bnc = 4#      Silence debounce interval (x10ms)
ttdata = 10#    DTMF tone duration (x10ms)
minpdon = 2#    Min on interval for pulse (x10ms)
minpdoff = 2#   Min off interval for pulse (x10ms)
minipd = 25#    Min interdigit time for pulse (x10ms)
minlcoff = 65535#  Min loop off duration (x10ms)
#   (Default is 65535=-1, which means "disabled")
maxpdoff = 50#  Max pulse make duration (x10ms)

INIT.DEF db_bases = 0         # Max number of active databases
db_recs = 0          # Max number of active database records
db_reclen = 0        # Max database record length
db_fields = 0        # Max fields in one database
db_bdes = 0          # Max active database descriptors
db_rdes = 0          # Max active record descriptors
msg_size = 100       # Max length of message string
msg_num = 100        # Max number of pending messages
glb_size = 32#  Max length of global variable
glb_num = 32#   Number of global variables
buf_num = 8#    Number of 1k buffers
fil_num = 20#   Max open DOS files
db_ixnum = 0#   Max number of active index files
db_ixkey = 0#   Max length of index key
db_ixcache = 0# Number of 1k cache buffers per index file
db_btrieve = 0# Btrieve support? 1=YES 0=NO
ser_buff = 1024      # COM port buffer size (bytes)
ser_ports = 2        # Number of COM ports to support (0 .. 4)
fil_buf = 0          # fil_copy() buffer size (Kb, or 9999=EMS)
sc_words = 0         # Max words in sc_playph or sc_playphm phrase
sc_nshgup = 0        # Continuous tone treated as hang-up 1=Yes 0=No
arg_size = 15        # Max chars in spawna/chain argument
fil_locks = 0        # Max active calls to fil_lock
log_size = 4096      # Max size of VOS?.LOG

PART.DEF

# PART.DEF  -  Memory partition definitions
# Test file....This may not be correct....

1    N    MASTER
1    N    CLOCK
1    N    WATCHDOG
16   N    INCOMING
16   N    OUTGOING

BTRVTMPL.TXT

CllInf {
    IDNumber          LI
    Passcode          LI
    FirstName         US    15
    MiddleName        US    15
    LastName          US    15
    Address1          US    40
```

```
    Address2              US   40
    City                  US   30
    State                 US    2
    ZipCode               US    9
    NoteLength            UI
    Notes                 US  200
}

LogCll {
    CallNumber            LI
    ProcessCode           US    1
    IDNumber              LI
    PrimaryPhoneNumber    US   30
    CallDate              US    6
    CallTime              US    6
    CallDuration          LI
    CallStatus            US   15
    CallAttempts          I
}

LogMsg {
    CallNumber            LI
    SequenceNumber        LI
    ProcessCode           US    1
    MessageID             US   16
    CompleteMessageID1    LI
    CompleteMessageID2    LI
    CompleteMessageID3    LI
    CompleteMessageID4    LI
    Response              US    5
    ResponseLength        I
    ValidResponse         US   16
}

MsgRsp {
    MessageID             US   16
    Response              US    5
    Points                I
    DescriptionLength     UI
    Description           US  200
}
```

I claim:

1. An automated and interactive positive motivation system comprising:
   a) means for recording and accessing a client's database that includes a client program which incorporates for each client, a calling schedule and personal identification number;
   b) means for reinforcing predetermined client behavior based upon said means for recording and accessing said clients database which includes for each client one of either specific motivational messages, stimuli or questions which are to be responded to by the client;
   c) a computer having means for accessing said client database and said client program, said computer producing in sequence, a digital telephone signal that corresponds to a client's telephone number, a digital client validation request signal and one of either said motivational messages, stimuli or questions of said means for reinforcing predetermined client behavior that are only sent if said client's validation request signal is responded to by the client with a valid personal identification number,
   (d) means for converting digital signals produced by said computer to telephone tone signals that are sent to a client's dual tone multifrequency telephone set via a telephone network where said telephone set is queued to respond to the client's validation request, hear said motivational messages and to respond to said questions;
   (e) means for converting telephone tone signals originating at said client's telephone set to digital signals for application to and processing by said computer; and
   (f) means for permanently recording all outgoing and incoming client communications.

2. The system as specified in claim 1 wherein said means for recording and accessing a client's database comprising a compact disc and a compact disc player interfacing with said computer.

3. The system as specified in claim 1 wherein said means for recording and accessing a client's program comprising a compact disc and a compact disc player that interfaces with said computer.

4. The system as specified in claim 1 wherein said computer comprising an IBM-AT compatible computer having an 80386 processor including a Dialogic D41 4-line speech card 5. The system as specified in claim 1 wherein said means for converting said digital signals from said computer to telephone tone signals comprising a digital/-telephone tone signal converter having circuit means for performing the conversion in either direction.

6. The system as specified in claim 1 wherein said means for reinforcing a client's program comprising an electronic weight scale that does not allow the client to view his/her weight.

7. The system specified in claim 1 wherein said means for reinforcing a client's program comprising an olfactory unit to provide smells in association with said client database.

8. The system specified in claim 1 wherein said means for reinforcing a client's program comprising a voice stress analyzer.

9. The system specified in claim 1 wherein said means for reinforcing a client's program comprising using an interactive television system.

10. The system specified in claim 1 wherein said means for reinforcing a client's program comprising an EEG measuring and recording device.

11. The system specified in claim 1 wherein said means for reinforcing a client's program comprising an interactive video system.

12. The system specified in claim 1 wherein said means for reinforcing a client's program addresses stored information from an optical disc.

13. A positive reinforcement and feedback system comprising:
   a) a client database that includes for each client the name, calling schedule and personal identification number,
   b) a reinforcing means for reinforcing client behavior by selecting information from said client database including a client program that for each client has specific motivational messages, stimuli or questions that are to be responded to by the client,
   c) a digital/telephone tone signal converter having circuit means for converting digital signals from said reinforcing means to corresponding telephone tone signals and telephone tone signals to corresponding digital signals,
   (d) a telephone network having circuit means for receiving said telephone tone signals from said converter and to transmit said tone signals to a client's dual tone multifrequency telephone set from where the client can receive and respond to one of either said specific motivational messages, stimuli or questions of said reinforcing means; and (e) a computer comprising in part a software program, a real-time clock and a logic network and integrated into said reinforcing means and said digital/telephone tone signal converter, wherein at preselected dates and times said computer program in combination with said logic network accesses said client database and said client program, whereupon if a match is found between said client's database and program, said computer in combination with said digital/telephone tone signal converter produce in sequence, a digital telephone signal that corresponds to the client's telephone number and a digital client validation request signal where said digital telephone signal and said digital client validation signal are applied to said converter from where said digital telephone signal and said digital client validation signal are converted to telephone tone signals corresponding to the client's telephone number and personal identification number, wherein the signals are then transmitted via said telephone network to said client's telephone set where the client can respond to the personal identification request, whereupon if the client responds back to said computer via said telephone network and said converter with a valid personal identification number by pressing on specific keys on a keypad of said dual tone multifrequency telephone set, said computer in combination with said software program and said logic network enables said client program to deliver one of either said messages, stimuli or questions of said reinforcing means to be transmitted via said telephone network to said client's telephone set where the client can receive one of either said messages, stimuli or questions of said reinforcing means and respond to said messages, stimuli or questions of said reinforcing means.

14. The system as specified in claim 13 wherein said computer is comprised of an IBM-AT compact computer having an 80386 processor including a Dialogic D41 4-line speech card.

15. The system as specified in claim 13 wherein said client's database is recorded on a compact disc (CD) recording that is played back to said computer by means of a CD player.

16. The system as specified in claim 13 wherein said client's database is recorded on a tape cartridge that is played back to said computer by means of a tape cartridge player.

17. The system as specified in claim 13 wherein said client's program is recorded on a compatible disc recording that is played back to said computer by means of a CD player.

18. The system as specified in claim 13 wherein said client's program is recorded on a tape cartridge that is played back to said computer by means of a tape cartridge player.

19. The system as specified in claim 13 wherein said telephone network consists of a private telephone network that operates within the confines of an enclosed area.

20. The system as specified in claim 13 wherein said client's dual tone multifrequency telephone set consists of a standard telephone set hardwired to said telephone network.

21. The system as specified in claim 13 wherein said client's dual tone multifrequency telephone set comprising a transportable/cellular telephone.

22. The system specified in claim 13 wherein said means for reinforcing a client's program comprising an EEG measuring and recording device.

23. The system specified in claim 13 wherein said means for reinforcing a client's program comprising an interactive video system.

24. The system specified in claim 13 wherein said means for reinforcing a client's program addressing stored information from an optical disc.

25. The system as specified in claim 13 wherein said means for reinforcing a client's program comprising an electronic weight scale having an enclosure which prevents the client from viewing his weight.

26. The system as specified in claim 13 wherein said means for reinforcing a client's program comprise an olfactory unit to providing smells indexed to said client data base.

27. The system as specified in claim 13 wherein said means for reinforcing a client's program comprising a voice stress analyzer.

28. The system as specified in claim 13 wherein said means for reinforcing a client's program comprising an interactive television system.

29. The system as specified in claim 13 further comprising:

a) a modem that is activated by a telephone signal produced by said digital/telephone tone converter via said telephone network, and b) means for receiving and recording the output of said modem, where the received data is subsequently received by the client for his or her review or response via said client's dual tone multifrequency telephone set.

30. The system as specified in claim 29 wherein said modem receiving and recording means includes a personal computer.

31. The system as specified in claim 29 wherein said modem receiving and recording means includes a printer.

32. The system as specified in claim 29 wherein said modem receiving and recording means includes a facsimile machine.

33. The system as specified in claim 29 further comprising a client-assigned alpha-numeric pager activated by a telephone signal produced by said telephone network, wherein the message received comprising a message requiring a response via the client's dual tone multifrequency telephone set.

34. The system as specified in claim 13 further comprising a two-way, interactive, computer-activated message display unit connected directly to said computer via said telephone network and said digital/telephone tone signal converter.

35. The system as specified in claim 13 further comprising an electronics scale having means for measuring the client's weight and reporting that weight to said computer via said telephone network and said digital/telephone tone signal converter.

36. The system as specified in claim 13 wherein said client database and client program are stored on a hard disc located within said computer.

37. The system as specified in claim 13 wherein said reinforcing means further comprises:

a) a telephone number redial circuit that allows a client's busy telephone number to be automatically redialed at selectable time intervals, and b) a random telephone number dialer circuit that allows client telephone numbers stored in said client's database to be randomly selected and called.

38. The system as specified in claim 13 further comprising a printer connected to said computer where said printer records all outgoing and incoming client communications.

39. A method for an automated and interactive positive motivation system comprising the steps of:
  (a) recording a client calling schedule and personal identification number for a client;
  (b) storing said recording of said client calling schedule and said personal identification number in a client database;
  (c) reinforcing client behavior by selecting information from said client database including a client program that for each client has specific motivational messages, stimuli or questions that are to be responded to by the client;
  (d) producing a digital telephone signal that corresponds to said recording and said storing of said personal identification number in accordance with said client calling schedule in said client database;
  (e) converting said produced digital telephone signal to telephone tone signals in correspondence to said recording and said storing of said personal identification number in accordance with said client calling schedule in said client database;
  (f) sending said telephone tone signals from said converting of said digital telephone signal in accordance to said recording and said storing of said client calling schedule in said client database to a client's dual tone multifrequency telephone set;
  (g) comparing said telephone tone signals from said converting of said digital telephone signal corresponding to said personal identification number in said client database to a client's telephone tone signal input wherein if a match is found, a program means delivers one of either said motivational messages, stimuli or questions to said client; and
  (h) processing said client's response to said motivational messages, stimuli or questions by said program means and permanently recording said client's response in said client database, whereby said client calling schedule in said client database is updated by said program means for producing and converting said digital telephone signal in accordance with said client calling schedule to deliver another set of said motivational messages, stimuli or questions to said client.

* * * * *